US008394387B1

(12) United States Patent
Leppla et al.

(10) Patent No.: US 8,394,387 B1
(45) Date of Patent: Mar. 12, 2013

(54) **RECOMBINANT MODIFIED *BACILLUS ANTHRACIS* PROTECTIVE ANTIGEN FOR USE IN VACCINES**

(75) Inventors: Stephen H. Leppla, Bethesda, MD (US); Mary Jo Rosovitz, Germantown, MD (US); John B. Robbins, New York, NY (US); Rachel Schneerson, Bethesda, MD (US); S. Dana Hsu, Bethesda, MD (US); Joseph Shiloach, Rockville, MD (US); Delia M. Ramirez, Bethesda, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 1560 days.

(21) Appl. No.: 11/831,860

(22) Filed: Jul. 31, 2007

Related U.S. Application Data

(62) Division of application No. 10/638,006, filed on Aug. 8, 2003, now Pat. No. 7,261,900.

(60) Provisional application No. 60/402,285, filed on Aug. 9, 2002.

(51) Int. Cl.
*A61K 39/07* (2006.01)
*A61K 39/02* (2006.01)
*A61K 39/00* (2006.01)
*A61K 38/00* (2006.01)

(52) U.S. Cl. ............... 424/246.1; 424/234.1; 424/185.1; 424/190.1; 424/184.1; 530/300; 530/324; 530/350

(58) Field of Classification Search .................. None
See application file for complete search history.

(56) References Cited

U.S. PATENT DOCUMENTS

| 3,710,795 A | 1/1973 | Higuchi |
| 5,840,312 A | 11/1998 | Mock et al. |
| 6,267,966 B1 | 7/2001 | Baillie |
| 2004/0076638 A1 | 4/2004 | Shiloach et al. |

OTHER PUBLICATIONS

Ellis (Vaccines, W.B. Saunders Company, Chapter 29, 1988, pp. 568-574).*
Boslego et al (Vaccines and Immunotherapy, 1991, Chapter 17).*
Ramirez et al (Journal of Industrial Microbiology & Biotechnology Apr. 2002, 28, p. 232-238).*
(Ramirez et al, Abstract of SIM Meeting, Nov. 1, 2001).*
Baillie et al., "The expression of the protective antigen of *Bacillus anthracis* in *Bacillus subtilis*," *J. Appl. Microbiol.* 84:741-746, 1998.
Benson et al., Identification of Residues Lining the Anthrax Protective Antigen Channel, *Biochem.* 37:3941-3948, 1998.
Boslego and Deal, in *Vaccines and Immunotherapy*, Chapter 17, pp. 211-223, 1991.
Coulson et al.,"*Bacillus anthracis* protective antigen expressed in *Salmonella typhimurium* SL3261 affords protection against anthrax spore challenge," *Vaccine* 12:1395-1401, 1994.
Creighton in *Proteins: Structures and Molecular Properties*, pp. 314-315, W.H. Freeman and Company, New York, 1984.
Creighton in *Protein Structure: A Practical Approach*, pp. 184-186, IRL Press at Oxford University Press, Oxford, England, 1989.
Ellis in *Vaccines*, W.B. Saunders Company, Chapter 29, pp. 568-574, 1988.
Farchaus et al., "Purification and characterization of the major surface array protein from the avirulent *Bacillus anthracis* Delta Sterne-1," *J. Bacteriol.* 177:2481-2489, 1995.
Farchaus et al., "Fermentation, purification, and characterization of protectivbe antigen from a recombinant, avirulent strain of *Bacillus anthracis*," *Appl. Environ. Microbiol.* 64:982-991, 1998.
Flick-Smith et al., "A Recombinant Carboxy-Terminal Domain of the Protective Antigen of *Bacillus anthracis* Protects Mice against Anthrax Infection," *Infection and Immunity* 70:1653-1656, 2002.
Fouet et al.,"*Bacillus anthracis* surface: capsule and S-layer," *J. Appl. Microbiol.* 87:251-255, 1999.
Gladstone, "Immunity to anthrax: protective antigen present in cell-free culture filtrates," *Br. J. Exp. Pathol.* 27:394-418, 1946.
Gupta et al., "Expression and purification of the recombinant protective antigen of *Bacillus anthracis*," *Protein Expr.Purif.* 16:369-376, 1999.
Hemila et al., "Improving the production of *E. coli* beta-lactamase in *Bacillus subtilis*: the effect of glucose, pH and temperature on the production level," *J. Biotechnol.* 26:245-56, 1992.
Iacono-Connors et al., "Expression of the *Bacillus anthracis* protective antigen gene by baculovirus and vaccinia virus recombinants," *Infect. Immun.* 58:366-372, 1990.
Ivins et al., "Comparative efficacy of experimental anthrax vaccine candidates against inhalation anthrax in rhesus macaques," *Vaccine* 16:1141-1148, 1998.
Ivins and Welkos, "Cloning and expression of the *Bacillus anthracis* protective antigen gene in *Bacillus subtilis*," *Infect. Immun..* 54-537-542, 1986.
Keppie et al., "The chemical basis of the virulence of *Bacillus anthracis*,IX, Its aggressins and their mode of action," *Br. J. Exp. Pathol.* 44:446-453, 1963.
Khanna et al., "Role of Residues Constituting the 2β1 Strand of Domain II in the Biological Activity of Anthrax Protective Antigen," *FEMS Microbiol. Lett.* 199:27-31, 2001.

(Continued)

*Primary Examiner* — Robert A Zeman
(74) *Attorney, Agent, or Firm* — Klarquist Sparkman, LLP

(57) ABSTRACT

The invention relates to improved methods of producing and recovering sporulation-deficient *B. anthracis* mutant stains, and for producing and recovering recombinant *B. anthracis* protective antigen (PA), especially modified PA which is protease resistant, and to methods of using of these PAs or nucleic acids encoding these PAs for eliciting an immunogenic response in humans, including responses which provide protection against, or reduce the severity of, *B. anthracis* bacterial infections and which are useful to prevent and/or treat illnesses caused by *B. anthracis*, such as inhalation anthrax, cutaneous anthrax and gastrointestinal anthrax.

13 Claims, 9 Drawing Sheets

OTHER PUBLICATIONS

Klimpel et al., "Anthrax Toxin Protective Antigen is Activated by a Cell Surface Protease with the Sequence Specificity and Catalytic Properties of Furin," *Proc. Natl. Acad. USA* 89:10277-10281, 1992.

Leppla, "Production and purification of anthrax toxin," *Methods Enzymol.* 165:103-116, 1988.

Leppla, "The anthrax toxin complex," In: Sourcebook of bacterial toxins (Alouf and Freer, eds.), pp. 277-302, Academic Press, Inc., San Diego, CA, 1991.

Leppla, "Anthrax toxins," In: Bacterial toxins and virulence factors in disease, Handbook of natural toxins (Moss et al., eds.), pp. 543-572, Dekker, New York, 1995.

Little et al., "Passive protection by polyclonal antibodies against *Bacillus anthracis* infection in guinea pigs," *Infect. Inunun.* 65:5171-5175, 1997.

Miller et al., "Production and purification of recombinant protective antigen and protective efficacy against *Bacillus anihracis*," *Lett. Appl. Microbiol.* 26:56-60, 1998.
Nosoh et al., in *Protein Stability and Stabilization Through Protein Engineering*, pp. 197-217, Ellis Horwood Limited, West Sussex, England, 1991.
Park and Leppla, "Optimized production and purification of *Bacillus anthracis* lethal factor," *Protein Expression and Purification* 18:293-302, 2000.
Pezard et al., "Protective Immunity Induced by *Bacillus anthracis* Toxin-Deficient Strains," *Infection and Immunity 63*:1369-1372, 1995.
Puziss et al., "Large-scale production of protective antigen of *Bacillus anthracis* anaerobic cultures," *Appl. Microbiol.* 11:330-334, 1963.
Reuvemy et al., "Search for correlates of protective immunity conferred by anthrax vaccine," *Infect. Immun.* 69:2888-2893, 2001.
Sharma et al., "Expression and purification of anthrax toxin protective antigen from *Escherichia coli," Protein Expr. Purif.* 7:33-38, 1996.
Simonen and Palva, "Protein secretion in *Bacillus* species," *Microbiol. Rev.* 57:109-137, 1993.
Singh et al., "A deleted variant of *Bacillus anthracis* protective antigen is non-toxic and blocks anthrax toxin action in vivo," *J. Biol. Chem.* 264:19103-19107, 1989.
Singh et al., "Study of immunization against anthrax with the purified recombinat protective antigen of *Bacillus anthracis," Infect. Immun.* 66:3447-3448, 1998.
Singh et al., "The chymotrypsin-sensitive site, FFD315, in anthrax toxin protective antigen is required for translocation of lethal factor," *J. Biol. Chem.* 269:29039-29046, 1994.
Thorne, "Genetics of *Bacillus anthracis*," In: Microbiology (Leive et al.eds), pp. 56-62, American Society for Microbiology, Washington, D.C., 1985.
Turnbull, "Anthrax vaccines: past, present, and future," *Vaccine* 9:533-539, 1991.
Varughese et al., "Identification of a Receptor-Binding Region within Domain 4 of the Protective Antigen Component of Anthrax Toxin," *Infection and Immunity 67*:1860-1865, 1999.
Vodkin and Leppla, "Cloning of the protective antigen gene of *Bacillus anthracis," Cell* 34:693-697, 1983.
Wang et al., "Human Monoclonal Antibodies that Neutralize Anthrax Toxin by inhibiting Heptamer Assembly," *Human Antibodies 13*:105-110, 2004.
Welkos et al., "Sequence and analysis of the DNA encoding protective antigen of *Bacillus anthracis," Gene* 69:287-300, 1988.
Wild et al., "Human Antibodies from Immunized Donors are Protective Against Anthrax Toxin in vivo," *Nature Biotechnol.*, pp. 1-2, 2003.

* cited by examiner

```
  1  EVKQENRLLN ESESSSQGLL GYYFSDLNFQ APMVVTSSTT GDLSIPSSEL
 51  ENIPSENQYF QSAIWSGFIK VKKSDEYTFA TSADNHVTMW VDDQEVINKA
101  SNSNKIRLEK GRLYQIKIQY QRENPTEKGL DFKLYWTDSQ NKKEVISSDN
151  LQLPELKQKS SITSAGPTVP DRDNDGIPDS LEVEGYTVDV KNKRTFLSPW
201  ISNIHEKKGL TKYKSSPEKW STASDPYSDF EKVTGRIDKN VSPEARHPLV
251  AAYPIVHVDM ENIILSKNED QSTQNTDSQT RTISKNTSTS RTHTSEVGGV
301  SAGFSNSNSS TVAIDHSLSL AGERTWAETM GLNTADTARL NANIRYVNTG
351  TAPIYNVLPT TSLVLGKNQT LATIKAKENQ LSQILAPNNY YPSKNLAPIA
401  LNAQDDFSST PITMNYNQFL ELEKTKQLRL DTDQVYGNIA TYNFENGRVR
451  VDTGSNWSEV LPQIQETTAR IIFNGKDLNL VERRIAAVNP SDPLETTKPD
501  MTLKEALKIA FGFNEPNGNL QYQGKDITEF DFNFDQQTSQ NIKNQLAELN
551  ATNIYTVLDK IKLNAKMNIL IRDKRFHYDR NNIAVGADES VVKEAHREVI
601  NSSTEGLLLN IDKDIRKILS GYIVEIEDTE GLKEVINDRY DMLNISSLRQ
651  DGKTFIDFKK YNDKLPLYIS NPNYKVNVYA VTKENTIINP SENGDTSTNG
701  IKKILIFSKK GYEIG
```

FIG. 7

```
  1  EVKQENRLLNESESSSQGLLGYYFSDLNFQAPMVVTSSTTGDLSIPSSEL   50
     ||||||||||||||||||||||||||||||||||||||||||||||||||
  1  EVKQENRLLNESESSSQGLLGYYFSDLNFQAPMVVTSSTTGDLSIPSSEL   50

51  ENIPSENQYFQSAIWSGFIKVKKSDEYTFATSADNHVTMWVDDQEVINKA  100
     ||||||||||||||||||||||||||||||||||||||||||||||||||
 51  ENIPSENQYFQSAIWSGFIKVKKSDEYTFATSADNHVTMWVDDQEVINKA  100

101  SNSNKIRLEKGRLYQIKIQYQRENPTEKGLDFKLYWTDSQNKKEVISSDN  150
     ||||||||||||||||||||||||||||||||||||||||||||||||||
101  SNSNKIRLEKGRLYQIKIQYQRENPTEKGLDFKLYWTDSQNKKEVISSDN  150

151  LQLPELKQKSSNSRKKRSTSAGPTVPDRDNDGIPDSLEVEGYTVDVKNKR  200
     ||||||||||      ||||||||||||||||||||||||||||||||||
151  LQLPELKQKSS......ITSAGPTVPDRDNDGIPDSLEVEGYTVDVKNKR  194

201  TFLSPWISNIHEKKGLTKYKSSPEKWSTASDPYSDFEKVTGRIDKNVSPE  250
     ||||||||||||||||||||||||||||||||||||||||||||||||||
195  TFLSPWISNIHEKKGLTKYKSSPEKWSTASDPYSDFEKVTGRIDKNVSPE  244

251  ARHPLVAAYPIVHVDMENIILSKNEDQSTQNTDSQTRTISKNTSTSRTHT  300
     ||||||||||||||||||||||||||||||||||||||||||||||||||
245  ARHPLVAAYPIVHVDMENIILSKNEDQSTQNTDSQTRTISKNTSTSRTHT  294

301  SEVHGNAEVHASFFDIGGSVSAGFSNSNSSTVAIDHSLSLAGERTWAETM  350
     |||             | |||||||||||||||||||||||||||||||
295  SEV.............GGVSAGFSNSNSSTVAIDHSLSLAGERTWAETM  330

351  GLNTADTARLNANIRYVNTGTAPIYNVLPTTSLVLGKNQTLATIKAKENQ  400
     ||||||||||||||||||||||||||||||||||||||||||||||||||
331  GLNTADTARLNANIRYVNTGTAPIYNVLPTTSLVLGKNQTLATIKAKENQ  380

401  LSQILAPNNYYPSKNLAPIALNAQDDFSSTPITMNYNQFLELEKTKQLRL  450
     ||||||||||||||||||||||||||||||||||||||||||||||||||
381  LSQILAPNNYYPSKNLAPIALNAQDDFSSTPITMNYNQFLELEKTKQLRL  430

451  DTDQVYGNIATYNFENGRVRVDTGSNWSEVLPQIQETTARIIFNGKDLNL  500
     ||||||||||||||||||||||||||||||||||||||||||||||||||
431  DTDQVYGNIATYNFENGRVRVDTGSNWSEVLPQIQETTARIIFNGKDLNL  480

501  VERRIAAVNPSDPLETTKPDMTLKEALKIAFGFNEPNGNLQYQGKDITEF  550
     ||||||||||||||||||||||||||||||||||||||||||||||||||
481  VERRIAAVNPSDPLETTKPDMTLKEALKIAFGFNEPNGNLQYQGKDITEF  530

551  DFNFDQQTSQNIKNQLAELNATNIYTVLDKIKLNAKMNILIRDKRFHYDR  600
     ||||||||||||||||||||||||||||||||||||||||||||||||||
531  DFNFDQQTSQNIKNQLAELNATNIYTVLDKIKLNAKMNILIRDKRFHYDR  580

601  NNIAVGADESVVKEAHREVINSSTEGLLLNIDKDIRKILSGYIVEIEDTE  650
     ||||||||||||||||||||||||||||||||||||||||||||||||||
581  NNIAVGADESVVKEAHREVINSSTEGLLLNIDKDIRKILSGYIVEIEDTE  630
```

FIG. 8A

```
651  GLKEVINDRYDMLNISSLRQDGKTFIDFKKYNDKLPLYISNPNYKVNVYA  700
     |||||||||||||||||||||||||||||||||||||||||||||||||
631  GLKEVINDRYDMLNISSLRQDGKTFIDFKKYNDKLPLYISNPNYKVNVYA  680

701  VTKENTIINPSENGDTSTNGIKKILIFSKKGYEIG  735
     ||||||||||||||||||||||||||||||||||
681  VTKENTIINPSENGDTSTNGIKKILIFSKKGYEIG  715
```

FIG. 8B

```
   1 ATGAAAAAAC GAAAAGTGTT AATACCATTA ATGGCATTGT CTACGATATT
  50 AGTTTCAAGC ACAGGTAATT TAGAGGTGAT TCAGGCAGAA GTTAAACAGG
 101 AGAACCGGTT ATTAAATGAA TCAGAATCAA GTTCCCAGGG GTTACTAGGA
 151 TACTATTTTA GTGATTTGAA TTTTCAAGCA CCCATGGTGG TTACCTCTTC
 201 TACTACAGGG GATTTATCTA TTCCTAGTTC TGAGTTAGAA AATATTCCAT
 251 CGGAAAACCA ATATTTTCAA TCTGCTATTT GGTCAGGATT TATCAAAGTT
 301 AAGAAGAGTG ATGAATATAC ATTTGCTACT TCCGCTGATA ATCATGTAAC
 351 AATGTGGGTA GATGACCAAG AAGTGATTAA TAAAGCTTCT AATTCTAACA
 401 AAATCAGATT AGAAAAGGA AGATTATATC AAATAAAAAT TCAATATCAA
 451 CGAGAAAATC CTACTGAAAA AGGATTGGAT TTCAAGTTGT ACTGGACCGA
 501 TTCTCAAAAT AAAAAGAAG TGATTTCTAG TGATAACTTA CAATTGCCAG
 551 AATTAAAACA AAAATCTTCG ATTACAAGTG CAGGACCTAC GGTTCCAGAC
 601 CGTGACAATG ATGGAATCCC TGATTCATTA GAGGTAGAAG GATATACGGT
 651 TGATGTCAAA AATAAAAGAA CTTTTCTTTC ACCATGGATT TCTAATATTC
 701 ATGAAAAGAA AGGATTAACC AAATATAAAT CATCTCCTGA AAAATGGAGC
 751 ACGGCTTCTG ATCCGTACAG TGATTTCGAA AAGGTTACAG GACGGATTGA
 801 TAAGAATGTA TCACCAGAGG CAAGACACCC CCTTGTGGCA GCTTATCCGA
 851 TTGTACATGT AGATATGGAG AATATTATTC TCTCAAAAAA TGAGGATCAA
 901 TCCACACAGA ATACTGATAG TCAAACGAGA ACAATAAGTA AAAATACTTC
 951 TACAAGTAGG ACACATACTA GTGAAGTAGG AGGAGTATCT GCAGGATTTA
1001 GTAATTCGAA TTCAAGTACG GTCGCAATTG ATCATTCACT ATCTCTAGCA
1051 GGGGAAAGAA CTTGGGCTGA ACAATGGGT TTAAATACCG CTGATACAGC
1101 AAGATTAAAT GCCAATATTA GATATGTAAA TACTGGGACG GCTCCAATCT
1151 ACAACGTGTT ACCAACGACT TCGTTAGTGT TAGGAAAAAA TCAAACACTC
1201 GCGACAATTA AAGCTAAGGA AAACCAATTA AGTCAAATAC TTGCACCTAA
1251 TAATTATTAT CCTTCTAAAA ACTTGGCGCC AATCGCATTA AATGCACAAG
```

FIG. 9A

```
1301  ACGATTTCAG TTCTACTCCA ATTACAATGA ATTACAATCA ATTTCTTGAG

1351  TTAGAAAAAA CGAAACAATT AAGATTAGAT ACGGATCAAG TATATGGGAA

1401  TATAGCAACA TACAATTTTG AAAATGGAAG AGTGAGGGTG GATACAGGCT

1451  CGAACTGGAG TGAAGTGTTA CCGCAAATTC AAGAAACAAC TGCACGTATC

1501  ATTTTTAATG GAAAGATTT  AAATCTGGTA GAAAGGCGGA TAGCGGCGGT

1551  TAATCCTAGT GATCCATTAG AAACGACTAA ACCGGATATG ACATTAAAAG

1601  AAGCCCTTAA AATAGCATTT GGATTTAACG AACCGAATGG AAACTTACAA

1651  TATCAAGGGA AAGACATAAC CGAATTTGAT TTTAATTTCG ATCAACAAAC

1701  ATCTCAAAAT ATCAAGAATC AGTTAGCGGA ATTAAACGCA ACTAACATAT

1751  ATACTGTATT AGATAAAATC AAATTAAATG CAAAAATGAA TATTTTAATA

1801  AGAGATAAAC GTTTTCATTA TGATAGAAAT AACATAGCAG TTGGGGCGGA

1851  TGAGTCAGTA GTTAAGGAGG CTCATAGAGA AGTAATTAAT TCGTCAACAG

1901  AGGGATTATT GTTAAATATT GATAAGGATA TAAGAAAAAT ATTATCAGGT

1951  TATATTGTAG AAATTGAAGA TACTGAAGGG CTTAAAGAAG TTATAAATGA

2001  CAGATATGAT ATGTTGAATA TTTCTAGTTT ACGGCAAGAT GGAAAAACAT

2051  TTATAGATTT TAAAAATAT  AATGATAAAT TACCGTTATA TATAAGTAAT

2101  CCCAATTATA AGGTAAATGT ATATGCTGTT ACTAAAGAAA ACACTATTAT

2151  TAATCCTAGT GAGAATGGGG ATACTAGTAC CAACGGGATC AAGAAAATTT

2201  TAATCTTTTC TAAAAAGGC  TATGAGATAG GATAA
```

RECOMBINANT MODIFIED *BACILLUS ANTHRACIS* PROTECTIVE ANTIGEN FOR USE IN VACCINES

RELATED APPLICATION

This is a divisional of U.S. application Ser. No. 10/638,006 filed Aug. 8, 2003 now U.S. Pat. No. 7,261,900, which claims the benefit under 35 USC §119(e) to Provisional Application No. 60/402,285 filed Aug. 9, 2002.

FIELD OF THE INVENTION

This invention relates to improved methods for preparing *Bacillus anthracis* mutants and for producing recombinant *Bacillus anthracis* protective antigen (PA) for use in vaccines.

BACKGROUND OF THE INVENTION

Anthrax, a potentially fatal disease, is caused by *Bacillus anthracis*. The virulence of this pathogen is mediated by a capsule of a poly-D-γ-glutamic acid and an exotoxin composed of three proteins (14, 16, 17). The three protein components are the protective antigen (PA, 82 KDa), lethal factor (LF, 90.2 KDa) and edema factor (EF, 88.8 KDa). These proteins, non-toxic by themselves, form lethal toxins when combined with an activated PA (16). The genes coding for these three protein components and the capsule are found in the endogenous plasmids pXO1 and pXO2, respectively (29).

The capsule of *Bacillus anthracis*, composed of poly-D-glutamic acid, serves as one of the principal virulence factors during anthrax infection. By virtue of its negative charge, the capsule is purported to inhibit host defence through inhibition of phagocytosis of the vegetative cells by macrophages. In conjunction with lethal factor (LF) and edema factor (EF), whose target cells include macrophages and neutrophils, respectively, the capsule allows virulent anthrax bacilli to grow virtually unimpeded in the infected host. Spores germinating in the presence of serum and elevated $CO_2$ release capsule through openings on the spore surface in the form of blebs which may coalesce before sloughing of the exosporium and outgrowth of the fully encapsulated vegetative cell. It has not been established that spore encapsulation plays a role in the early events of anthrax infection. The capsule appears exterior to the S-layer of the vegetative cell and does not require the S-layer for its attachment to the cell surface.

There is only indirect evidence, albeit extensive, identifying the components of vaccin-induced immunity to anthrax and there is evidence that anti-PA neutralizing antibody titers can be a reliable surrogate marker for protective immunity (23). The protective antigen (PA), seems to be an essential component of all vaccines for anthrax (7, 18, 30): both mono and polyclonal antibodies to PA neutralize the anthrax toxin and confer immunity to *B. anthracis* in animal models. The US licensed vaccine for anthrax "Anthrax Vaccine Adsorbed" (AVA) is produced from the formalin-treated culture supernatant of *B. anthracis* Sterne strain, V770-NP1-R (pXO1+, pXO2−), adsorbed onto aluminum hydroxide (22). Although AVA has been shown to be effective against cutaneous infection in animals and humans and against inhalation anthrax by rhesus monkeys (12), it has several limitations: 1) AVA elicits relatively high degree of local and systemic adverse reactions probably mediated by variable amounts of undefined bacterial products, making standardization difficult; 2) the immunization schedule requires administration of six doses within an eighteen-month period, followed by annual boosters for those at risk; and 3) there is no defined vaccine-induced protective level of serum PA to evaluate new lots of vaccines.

Development of a well-characterized, standardized, effective and safe vaccine that would require fewer doses to confer immunity to both inhalational and cutaneous anthrax is needed (9, 30). It has been suggested that a vaccine composed of modified purified recombinant PA would be effective, safer, allow precise standardization, and probably would require fewer injections (27). Such a PA can be designed to be biologically inactive, more stable, and still maintained high immunogenicity.

In the examples herein, we describe the development of a production and purification process for recombinant PA from the non-sporogenic avirulent *B. anthracis* BH445 (pXO1−, pXO2−) strain. Following an 18-hour fermentation and three purification steps, large quantities of protective antigen suitable for vaccine production were obtained. The purified PA was tested in mice and was able to elicit neutralizing antibodies (for related disclosure, see U.S. Provisional Application 60/344,505, filed Nov. 9, 2001, incorporated herein by reference).

SUMMARY OF THE INVENTION

This invention relates to improved methods of preparing *Bacillus anthracis* protective antigen (PA).

The invention also relates to PA and/or compositions thereof, which are useful for inducing or eliciting an immunogenic response in mammals, including responses that provide protection against, or reduce the severity of, infections caused by *B. anthracis*. In particular, the invention relates to methods of using PA, and/or compositions thereof, to induce or elicit serum antibodies which have neutralizing activity against *B. anthracis* toxin. PA and/or compositions thereof are useful as vaccines to induce serum antibodies which are useful to prevent, treat or reduce the severity of infections caused by *B. anthracis*, such as inhalation anthrax, cutaneous anthrax and/or gastrointestinal anthrax.

The invention also relates to nucleic acids encoding PA of *B. anthracis*, and compositions thereof, which produce PA in sufficient amounts to be useful as pharmaceutical compositions or vaccines to induce serum antibodies for preventing and/or treating illnesses caused by *B. anthracis*. The invention also relates to suitable expression systems, viral particles, vectors, vector systems, and transformed host cells containing those nucleic acids.

The invention also relates to antibodies which immunoreact with the PA of *B. anthracis*, and/or compositions thereof. Such antibodies may be isolated, or may be provided in the form of serum containing these antibodies.

The invention also relates to pharmaceutical compositions and/or vaccines comprising at least one of the PAs, nucleic acids, viral particles, vectors, vector systems, transformed host cells or antibodies of the invention.

The invention also relates to methods for the prevention or treatment of *B. anthracis* infection n a mammal, by administration of pharmaceutical or vaccine compositions of the invention.

The invention also provides kits comprising one or more of the agents of the invention which are useful for vaccinating mammals for the treatment or prevention of *B. anthracis* infection.

5). (a) PA production (mg/g cells) λSNKE, ■ N657A; proteolytic activity μSNKE, ☐ N657A; (b) SDS-PAGE analysis of partially purified PA-N657A (SEQ ID NO: 5) and PA-SNKE-ΔFF-E308D (SEQ ID NO: 4).

Figure 2:
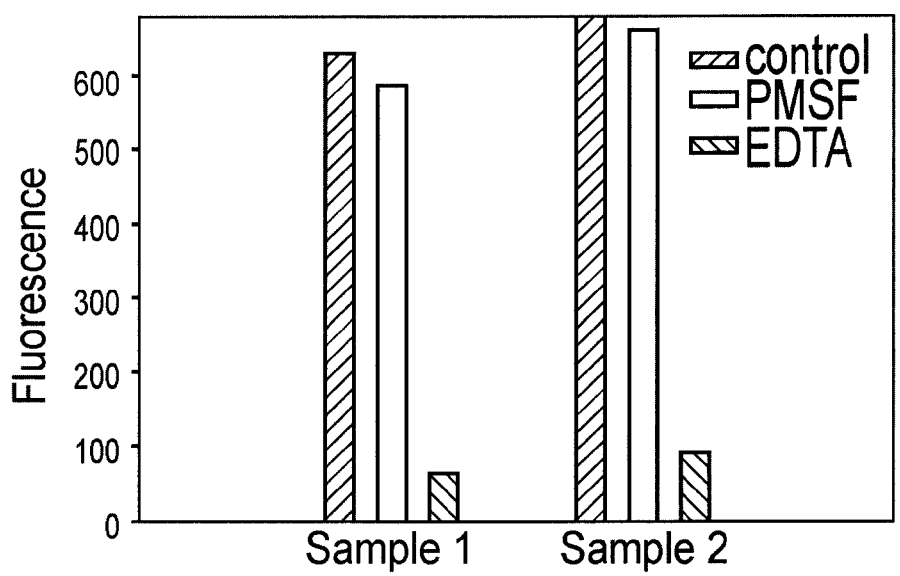

FIG. 2. Effect of EDTA and PMSF on proteolytic activity. Supernatants from two different cultures taken after 24 hours of growth were analyzed without inhibitors (control), with 1 μg/μL PMSF, and with 15 mM EDTA. Fluorescence is proportional to proteolytic activity.

Figure 3:
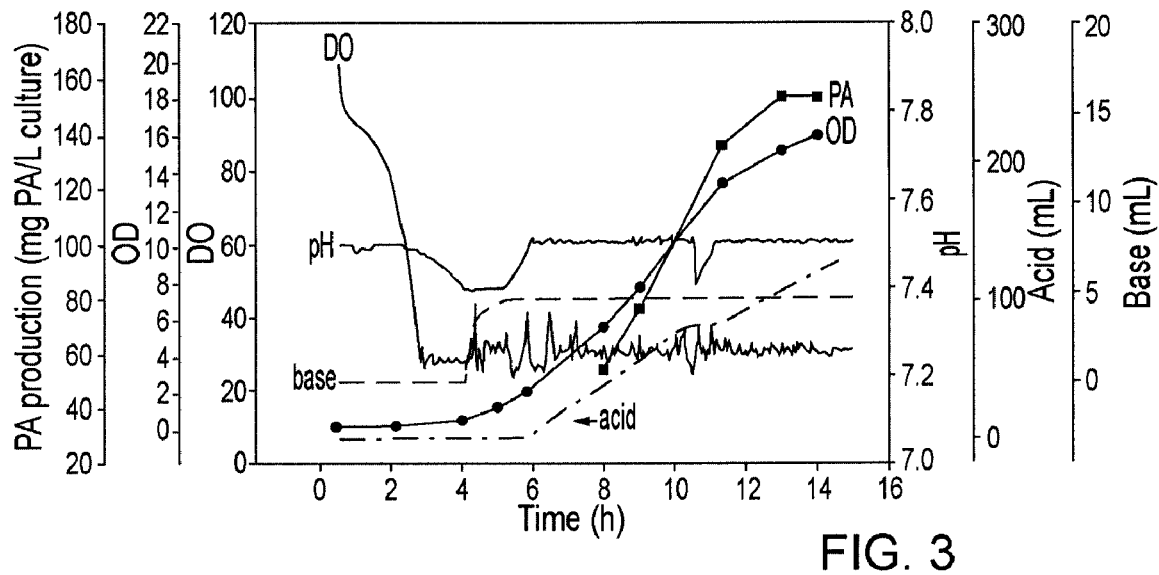

FIG. 3. Fermentation process for the production of PA-SNKE-ΔFF-E308D (SEQ ID NO: 4) from *B. anthracis* BH445. Acid and base values are cumulative.

Figure 4:
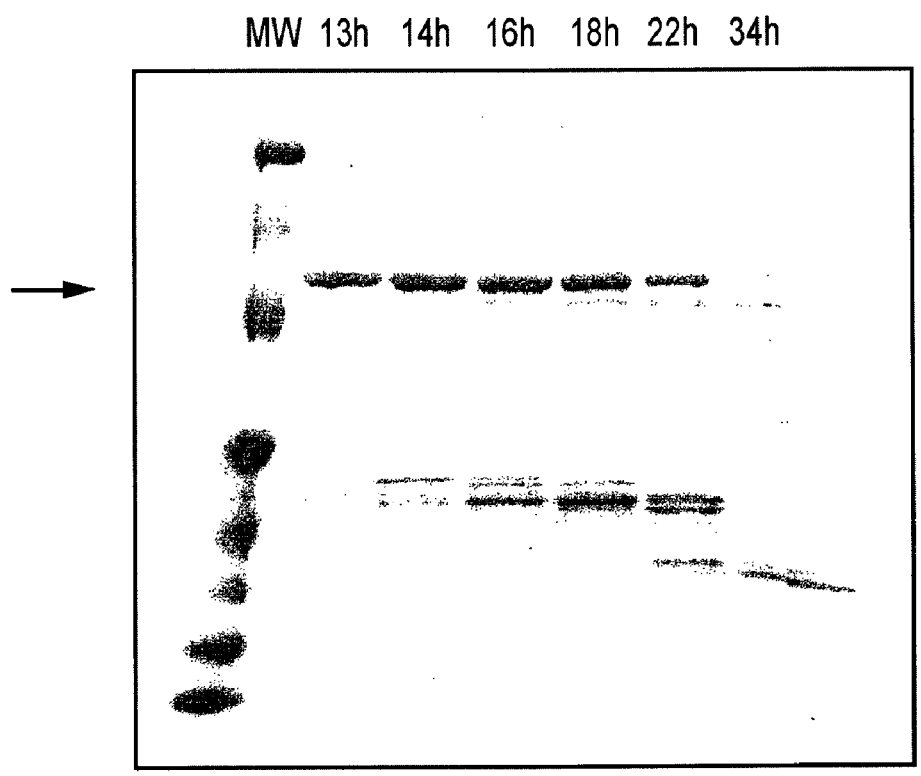

FIG. 4. SDS-PAGE analysis of culture supernatants obtained throughout the fermentation. Samples were taken at 13, 14, 16, 18, 22, and 34 hours of growth. Arrow indicates the location of PA (83 KDa) in the gel.

Figure 5:
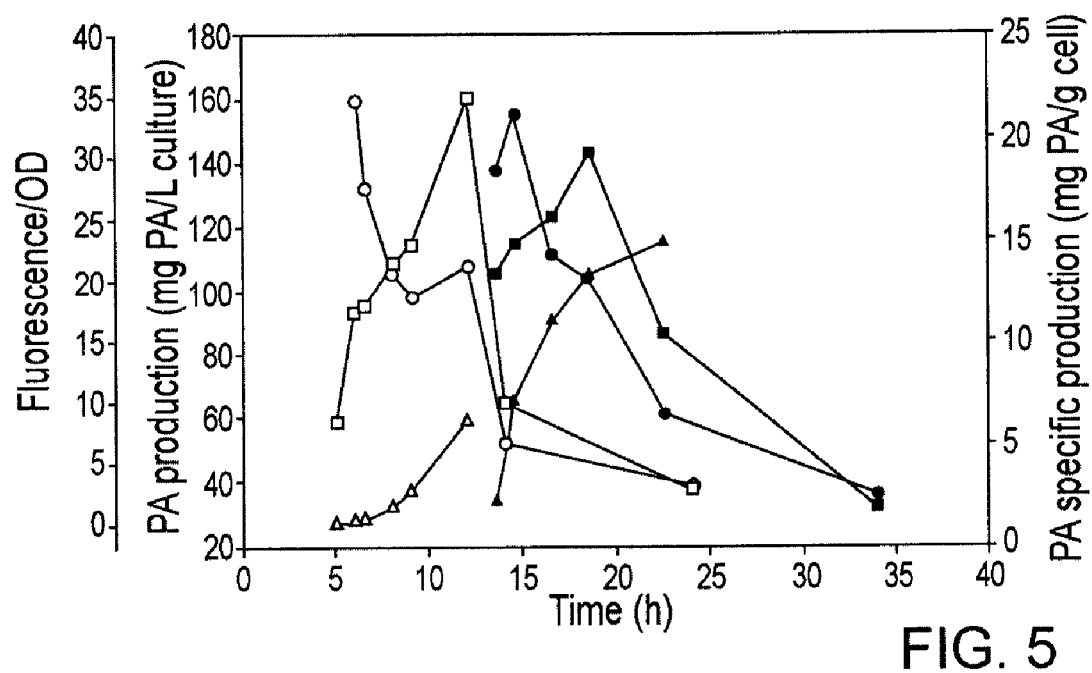

FIG. 5. PA production and proteolytic activity of *B. anthracis* BH445 [pSY5:SNKE-ΔFF-E308D; SEQ ID NO: 4] in fed-batch cultures supplied with tryptone/yeast extract or glucose. λ Specific PA production in tryptone/yeast extract (mg/g cells); ν Volumetric PA production in tryptone/yeast extract (mg/liter); σ Proteolytic activity in tryptone/yeast extract; μ Specific PA production in glucose (mg/g cells); ☐ Volumetric PA production in glucose (mg/liter); Δ Proteolytic activity in glucose.

Figure 6:
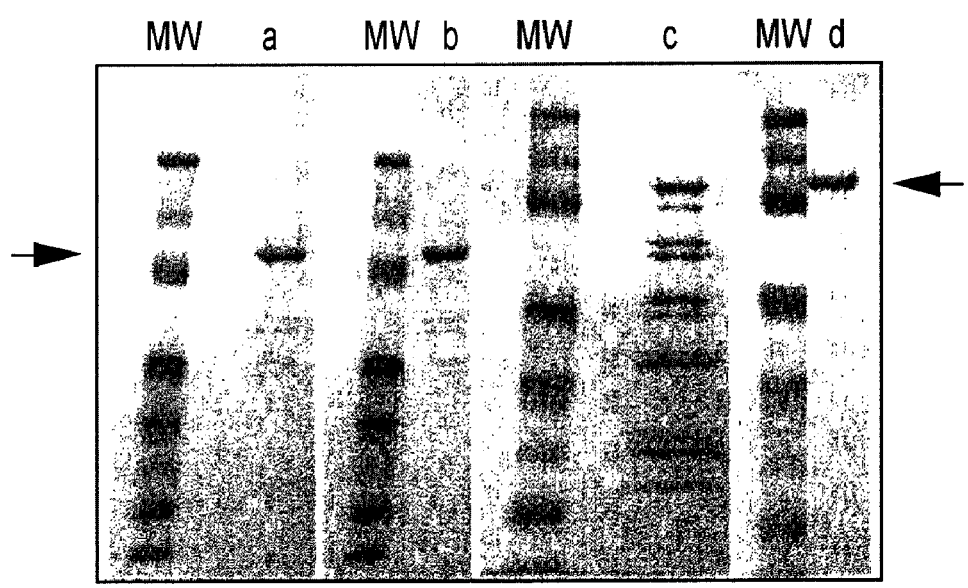

FIG. 6. SDS-PAGE analysis of purified PA fractions. (a) PA purified by packed bed chromatography; (b) PA after hydrophobic interaction chromatography and gel filtration; (c) PA fraction shown in Lane (b) after 3 months; (d) PA after expanded bed hydrophobic interaction chromatography, anion exchange, and gel filtration. MW indicates molecular weight markers. Arrows indicate the location of PA (83 KDa) in the gel.

FIG. 7. Exemplary amino acid sequence of a double mutant rPA (SEQ ID NO: 1). The double mutant modification was accomplished by: (a) deletion of residues 162 through 167 and the substitution of Ile for Ser at residue 168; (b) the deletion of residues 304-317 and the substitution of Gly for Ser at residue 319 (see FIGS. 7 and 8). The changes made in (a) remove the furin-cleavage loop, while the changes in (b) substitute two Gly residues for the entire chymotrypsin-cleavage loop.

FIGS. 8A and 8B. Amino acid sequence alignment of wild-type PA protein (upper sequence; SEQ ID NO: 2) and the exemplary double mutant PA protein shown in FIG. 7 (lower sequence; SEQ ID NO: 1).

FIGS. 9A and 9B. Nucleotide sequence of an exemplary polynucleotide (SEQ ID NO: 3) encoding the double mutant rPA shown in FIGS. 7, 8A and 8B.

SEQUENCE LISTING

SEQ ID NO: 1 is a protein sequence showing an exemplary double mutant PA.

SEQ ID NO: 2 is a protein sequence showing a wild-type PA protein.

SEQ ID NO: 3 is a nucleic acid coding sequence of SEQ ID NO: 1.

SEQ ID NO: 4 is a protein sequence showing the PA-SNKE-ΔFF-E308D mutant.

SEQ ID NO: 5 is a protein sequence showing the PA-N657A mutant.

DETAILED DESCRIPTION OF ILLUSTRATIVE EMBODIMENTS

It is to be understood that both the foregoing general description and the following detailed description are exemplary and explanatory only, and are not restrictive of the invention, as claimed. The accompanying drawings, which are incorporated in and constitute a part of the specification, illustrate an embodiment of the invention and, together with the description, serve to explain the principles of the invention.

The invention relates to methods of producing and recovering PA from a cell or organism, particularly a recombinant cell or microorganism. Exemplified herein is the production and purification of modified PA from a non-sporgenic strain of *Bacillus anthracis*. As discussed further herein, greater quantities of PA are obtainable from these cells or microorganisms than were obtainable by previously described methods.

The invention also relates to PA, and/or compositions thereof, which are useful for eliciting an immunogenic response in mammals, in particular humans, including responses which provide protection against, or reduce the severity of, infections caused by *B. anthracis*. The invention also relates to methods of using such PA, and/or compositions thereof, to induce serum antibodies against PA. PA, and/or compositions thereof, are useful as vaccines to induce serum antibodies that are useful to prevent, treat or reduce the severity of infections caused by *B. anthracis*, such as inhalation anthrax and/or cutaneous anthrax. The PAs of this invention are expected to induce a strong protective IgG antibody response in mammals, including humans.

The invention also relates to nucleic acids encoding PA and mutant forms of PA of this invention. Nucleic acids encoding PA, and compositions thereof, are also useful as pharmaceutical compositions or vaccines to induce serum antibodies that are useful to prevent and/or treat illnesses caused by *B. anthracis*.

The invention also relates to antibodies which immunoreact with the PA of *B. anthracis* that are induced by PAs of the invention, and/or compositions thereof. Such antibodies may be isolated, or may be provided in the form of serum containing these antibodies.

The invention also relates to a method for the prevention or treatment of *B. anthracis* infection in a mammal, by administration of compositions containing one or more of a PA of the invention, nucleic acids encoding a PA if the invention, antibodies and/or serum containing antibodies of the invention.

The invention also provides kits for vaccinating mammals for the treatment or prevention of *B. anthracis* infection in a mammal comprising one or more of the agents of the invention.

The present invention also encompasses methods of using mixtures of one or more of the PA, nucleic acids, and/or antibodies of the invention, either in a single composition or in multiple compositions containing other immunogens, to form a multivalent vaccine for broad coverage against either *B. anthracis* itself or a combination of *B. anthracis* and one or more other pathogens, which may also be administered concurrently with other vaccines, such as the DTP vaccine.

Pharmaceutical compositions of this invention are capable, upon injection into a human, of inducing serum antibodies against *B. anthracis*. The induced anti-PA antibodies have anthrax toxin neutralizing activity which are preferably at least comparable to those induced by the currently licensed anthrax vaccine.

The vaccines of this invention are intended for active immunization for prevention of *B. anthracis* infection, and for preparation of immune antibodies. The vaccines of this invention are designed to confer specific immunity against infection with *B. anthracis*, and to induce antibodies specific to *B. anthracis* PA. The *B. anthracis* vaccine is composed of non-toxic bacterial components, suitable for infants, children of all ages, and adults.

The methods of using the agents of this invention, and/or compositions thereof will be useful in increasing resistance to, preventing, ameliorating, and/or treating *B. anthracis* infection in humans.

This invention also provides compositions, including but not limited to, mammalian serum, plasma, and immunoglobulin fractions, which contain antibodies which are immunoreactive with *B. anthracis* PA. These antibodies and antibody compositions may be useful to prevent, treat, and/or ameliorate infection and disease caused by the microorganism. The invention also provides such antibodies in isolated form.

High titer anti-PA sera, or antibodies isolated therefrom, may be used for therapeutic treatment for patients with *B. anthracis* infection. Antibodies elicited by the agents of this invention may be used for the treatment of established *B. anthracis* infections, and may also be useful in providing passive protection to an individual exposed to *B. anthracis*.

The present invention also provides kits comprising vaccines for the prevention and/or treatment of *B. anthracis*, containing the one or more of the PAs, nucleic acids, viral particles, vectors, vector systems, or transformed host cells or antibodies of the invention and/or compositions thereof. The PAs, nucleic acids viral particles vectors, host cells and/or antibodies of the present invention may be isolated and purified by methods known in the art. Preferably, the PA of the invention is purified by one of the methods exemplified herein.

The vaccines of the invention are intended to be included in the immunization schedule of individuals at risk for *B. anthracis* infection. They are also planned to be used for intervention in the event of the use of *B. anthracis* in bioterrorism or biowarfare. For example, it is anticipated that the vaccines of the invention may be provided to the entire U.S. population. Additionally, they may be used as component(s) of a, multivalent vaccine for *B. anthracis* and/or other pathogens.

DEFINITIONS

As used herein, unless otherwise specifically noted, "PA" refers to all forms of PA which are useful in the compositions and/or methods of the invention, including unmodified native or recombinant *B. anthracis* protective antigen (PA), or a modified form (variant) or fragment thereof, for use in vaccines. Variants and fragments of PA must be able to produce an immune response in a mammal to whom they are administered. The immune response is suitably protective against infection by *Bacillus anthracis* although the protective effect may be seen only after repeated applications, as would be determinable by methods known in the art. Modified PA variants comprise peptides and proteins which resemble PA in their ability to induce or elicit antibodies which bind to native PA, but have different amino acid sequence. For example, variants may be 60% homologous to PA protein, suitably 80% homologous and more particularly at least 90% homologous. Fragments are suitably peptides that contain at least one antigenic determinant of PA.

A modified (variant) PA of the invention includes any substituted analog or chemical derivative of PA, so long as the modified (variant) PA is capable of inducing or eliciting the production of antibodies capable of binding native (or naturally-occurring) PA. Preferably, the antibodies are neutralizing antibodies. PA can be subject to various changes that provide for certain advantages in its use. For example, PA with changes which increase in vitro and/or in vivo stability of PA, while still retaining the desired immunogenic activity, are preferred. In the modified PA used in the examples herein (SEQ ID NO: 4), two regions were altered, i.e., the furin cleavage site region ($RKKR^{167}$ to $SNKE^{167}$), and the chymotrypsin and thermolysin cleavage site region (two Phe at positions 313-314 were deleted and Glu acid at position 308 was substituted with Asp), resulting in a more stable PA. As used herein, the terms "immunoreact" and "immunoreactivity" refer to specific binding between an antigen or antigenic determinant-containing molecule and a molecule having an antibody combining site, such as a whole antibody molecule or a portion thereof.

As used herein, the term "antibody" refers to immunoglobulin molecules and immunologically active portions of immunoglobulin molecules. Exemplary antibody molecules are intact immunoglobulin molecules, substantially intact immunoglobulin molecules and portions of an immunoglobulin molecule, including those portions known in the art as Fab, Fab', $F(ab')_2$ and F(v), as well as chimeric antibody molecules.

As used herein, the term "transduction" generally refers to the transfer of genetic material into the host via infection, e.g., in this case by the lentiviral vector. The term "transfection" generally refers to the transfer of isolated genetic material into cells via the use of specific transfection agents (e.g., calcium phosphate, DEAE Dextran, lipid formulations, gold particles, and other microparticles) that cross the cytoplasmic membrane and deliver some of the genetic material into the cell nucleus.

Monomers, Polymers and Polymeric Carriers

The present invention encompasses monomers of PA, as well as homogeneous or heterogeneous polymers of PA (e.g., concatenated, cross-linked and/or fused identical polypeptide units or concatenated, cross-linked and/or fused diverse peptide units), and mixtures of the polypeptides, polymers, and/or conjugates thereof. The present invention also encompasses PA bound to a non-toxic, preferably non-host, protein carrier to form a conjugate.

Linkers useful in the invention may, for example, be simply peptide bonds, or may comprise amino acids, including amino acids capable of forming disulfide bonds, but may also comprise other molecules such as, for example, polysaccharides or fragments thereof.

The linkers for use with this invention may be chosen so as to contribute their own immunogenic effect which may be either the same, or different, than that elicited by the consensus sequences of the invention. For example, such linkers may be bacterial antigens which also elicit the production of antibodies to infectious bacteria. In such instances, for example, the linker may be a protein or protein fragment of an infectious bacteria.

Carriers are chosen to increase the immunogenicity of the PA and/or to raise antibodies against the carrier which are medically beneficial. Carriers that fulfill these criteria are well known in the art. A polymeric carrier can be a natural or a synthetic material containing one or more functional groups, for example primary and/or secondary amino groups, azido groups, or carboxyl groups. Carriers can be water soluble or insoluble.

Methods for Attaching PA to a Protein Carrier

PA of the invention may be covalently attached to other proteins, with or without a linker, by methods known in the art, such as via their side chains or via peptide bonds in the primary chain. Cysteine molecules may provide a convenient attachment point through which to chemically conjugate other proteins or non-protein moieties to PA.

Dosage for Vaccination

The pharmaceutical compositions of this invention contain a pharmaceutically and/or therapeutically effective amount of at least one PA, nucleic acid, vector, viral particle, host cell immunogen or antibody of the invention. The effective amount of immunogen per unit dose is an amount sufficient to induce an immune response which is sufficient to prevent, treat or protect against the adverse effects of infection with *B. anthracis*. The effective amount of immunogen per unit dose depends, among other things, on the species of mammal inoculated, the body weight of the mammal and the chosen inoculation regimen, as is well known in the art.

In such circumstances, inocula for a human or similarly sized mammal typically contain PA concentrations of 0.5 µg to 1 mg per mammal per inoculation dose. Initial tests of the PA vaccine in humans will use approximately 10 µg or 20 µg per dose. Preferably, the route of inoculation of the peptide will be subcutaneous or intramuscular. The dose is administered at least once.

To monitor the antibody response of individuals administered the compositions of the invention, antibody levels may be determined. In most instances it will be sufficient to assess the antibody titer in serum or plasma obtained from such an individual. Decisions as to whether to administer booster inoculations or to change the amount of the composition administered to the individual may be at least partially based on the level.

The level may be based on either an immunobinding assay which measures the concentration of antibodies in the serum which bind to a specific antigen, i.e. PA. The ability to neutralize in vitro and in vivo biological effects of the *B. anthracis* toxins may also be assessed to determine the effectiveness of the treatment.

The term "unit dose" as it pertains to the inocula refers to physically discrete units suitable as unitary dosages for mammals, each unit containing a predetermined quantity of active material calculated to produce the desired immunogenic effect in association with the required diluent.

Inocula are typically prepared in physiologically and/or pharmaceutically tolerable (acceptable) carrier, and are preferably prepared as solutions in physiologically and/or pharmaceutically acceptable diluents such as water, saline, phosphate-buffered saline, or the like, to form an aqueous pharmaceutical composition. Adjuvants, such as aluminum hydroxide, may also be included in the compositions.

Depending on the intended mode of administration, the compounds of the present invention can be in various pharmaceutical compositions. The compositions will include, as noted above, an effective amount of the selected immunogen and/or antibody of the invention in combination with a pharmaceutically acceptable carrier and, in addition, may include other medicinal agents, pharmaceutical agents, carriers, adjuvants, diluents, etc. By "pharmaceutically acceptable" is meant a material that is not biologically or otherwise undesirable, i.e., the material may be administered to an individual along with the immunogen and/or antibody or other composition without causing any undesirable biological effects or interacting in a deleterious manner with any of the other components of the pharmaceutical composition in which it is contained.

The route of inoculation may be intramuscular, subcutaneous or the like, which results in eliciting antibodies protective against *B. anthracis*. In order to increase the antibody level, a second or booster dose may be administered approximately 4 to 6 weeks after the initial injection. Subsequent doses may be administered as indicated herein, or as desired by the practitioner.

Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, which is incorporated by reference herein.

Antibodies

An antibody of the present invention in one embodiment is characterized as comprising antibody molecules that immunoreact with *B. anthracis* PA.

An antibody of the present invention is typically produced by immunizing a mammal with an immunogen or vaccine containing an *B. anthracis* PA to induce, in the mammal, antibody molecules having immunospecificity for the immunizing PA. Antibody molecules having immunospecificity for the protein carrier will also be produced. The antibody molecules may be collected from the mammal and, optionally, isolated and purified by methods known in the art.

Human or humanized monoclonal antibodies are preferred, including those made by phage display technology, by hybridomas, or by mice with human immune systems. The antibody molecules of the present invention may be polyclonal or monoclonal. Monoclonal antibodies may be produced by methods known in the art. Portions of immunoglobulin molecules, such as Fabs, may also be produced by methods known in the art.

The antibody of the present invention may be contained in blood plasma, serum, hybridoma supernatants and the like. Alternatively, the antibodies of the present invention are isolated to the extent desired by well-known techniques such as, for example, ion exchange chromatography, sizing chromatography, or affinity chromatography. The antibodies may be purified so as to obtain specific classes or subclasses of antibody such as IgM, IgG, IgA, $IgG_1$, $IgG_2$, $IgG_3$, $IgG_4$ and the like. Antibodies of the IgG class are preferred for purposes of passive protection. The antibodies of the present invention have a number of diagnostic and therapeutic uses. The antibodies can be used as an in vitro diagnostic agent to test for the presence of *B. anthracis* in biological samples or in meat and meat products, in standard immunoassay protocols. Such assays include, but are not limited to, agglutination assays, radioimmunoassays, enzyme-linked immunosorbent assays, fluorescence assays, Western blots and the like. In one such assay, for example, the biological sample is contacted first with antibodies of the present invention which bind to *B. anthracis* PA, and then with a labeled second antibody to detect the presence of *B. anthracis* to which the first antibodies have bound.

Such assays may be, for example, of direct format (where the labeled first antibody is reactive with the antigen), an indirect format (where a labeled second antibody is reactive with the first antibody), a competitive format (such as the addition of a labeled antigen), or a sandwich format (where both labeled and unlabelled antibody are utilized), as well as other formats described in the art.

The antibodies of the present invention are also useful in prevention and treatment of infections and diseases caused by *B. anthracis*.

In providing the antibodies of the present invention to a recipient mammal, preferably a human, the dosage of administered antibodies will vary depending upon such factors as the mammal's age, weight, height, sex, general medical condition, previous medical history and the like.

In general, it is desirable to provide the recipient with a dosage of antibodies that is in the range of from about 1 mg/kg to about 10 mg/kg body weight of the mammal, although a lower or higher dose may be administered. The antibodies of the present invention are intended to be provided to the recipient subject in an amount sufficient to prevent, or lessen or attenuate the severity, extent or duration of the infection by *B. anthracis*. When proteins of other organisms are used as carriers, antibodies which immunoreact with those proteins are intended to be provided to the recipient subject in an amount sufficient to prevent, lessen or attenuate the severity, extent or duration of an infection by the organisms producing those proteins.

The administration of the agents of the invention may be for either "prophylactic" or "therapeutic" purpose. When provided prophylactically, the agents are provided in advance of any symptom. The prophylactic administration of the agent serves to prevent or ameliorate any subsequent infection. When provided therapeutically, the agent is provided at (or shortly after) the onset of a symptom of infection. The agent of the present invention may, thus, be provided prior to the anticipated exposure to *B. anthracis*, so as to attenuate the anticipated severity, duration or extent of an infection and disease symptoms, after exposure or suspected exposure to these bacteria, or after the actual initiation of an infection.

For all therapeutic, prophylactic and diagnostic uses, one or more of the PAs or other agents of this invention, as well as antibodies and other necessary reagents and appropriate devices and accessories, may be provided in kit form so as to be readily available and easily used.

Nucleic Acids, Vectors and Hosts

Nucleic acids encoding the PAs of the invention can be introduced into a vector such as a plasmid, cosmid, phage, virus, viral particle or mini-chromosome and inserted into a host cell or organism by methods well known in the art. The vectors which can be utilized to clone and/or express these nucleic acids are the vectors which are capable of replicating and/or expressing the nucleic acids in the host cell in which the nucleic acids are desired to be replicated and/or expressed. See, e.g., F. Ausubel et al., Current Protocols in Molecular Biology, Greene Publishing Associates and Wiley-Interscience (1992) and Sambrook et al. (1989) for examples of appropriate vectors for various types of host cells. Vectors and compositions for enabling production of the peptides in vivo, i.e., in the individual to be treated or immunized, are also within the scope of this invention. Strong promoters compatible with the host into which the gene is inserted may be used. These promoters may be inducible. The host cells containing these nucleic acids can be used to express large amounts of the protein useful in pharmaceuticals, diagnostic reagents, vaccines and therapeutics. Vectors include retroviral vectors and also include direct injection of DNA into muscle cells or other receptive cells, resulting in the efficient expression of the peptide, using the technology described, for example, in Wolff et al., Science 247:1465-1468 (1990), Wolff et al., Human Molecular Genetics 1(6):363-369 (1992) and Ulmer et al., Science 259:1745-1749 (1993). See also, for example, WO 96/36366 and WO 98/34640.

In general, vectors containing nucleic acids encoding PA can be utilized in any cell, either eukaryotic or prokaryotic, including mammalian cells (e.g., human (e.g., HeLa), monkey (e.g., COS), rabbit (e.g., rabbit reticulocytes), rat, hamster (e.g., CHO and baby hamster kidney cells) or mouse cells (e.g., L cells), plant cells, yeast cells, insect cells or bacterial cells (e.g., *E. coli*)). However, bacterial vectors and host cells are preferred in the present invention.

There are numerous *E. coli* expression vectors known to one of ordinary skill in the art useful for the expression of PA. Other microbial hosts suitable for use include bacilli, such as *B. subtilus*, and other enterobacteriaceae, such as *Salmonella, Serratia*, and various *Pseudomonas* species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary an amino terminal methionine can be provided by insertion of a Met codon 5' and in-frame with the antigen. Also, if desired, the carboxy-terminal or other region of the antigen can be removed using standard oligonucleotide mutagenesis procedures.

The nucleotide (DNA) sequences can be expressed in hosts after the sequences have been operably linked to, i.e., positioned to ensure the functioning of, an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired DNA sequences (see, e.g., U.S. Pat. No. 4,704,362).

Host bacterial cells may be chosen that are mutated to be reduced in or free of proteases, so that the proteins produced are not degraded. For *bacillus* expression systems in which the proteins are secreted into the culture medium, strains are available that are deficient in secreted proteases.

Polynucleotides encoding a variant polypeptide may include sequences that facilitate transcription (expression sequences) and translation of the coding sequences such that the encoded polypeptide product is produced. Construction of such polynucleotides is well known in the art. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

Fermentation and Purification Procedures

This invention relates to improved methods of preparing *B. anthracis* PA for use in vaccines. Procedures are exemplified herein for purifying modified PA from a protease-deficient nonsporogenic avirulent strain of *B. anthracis*. However, it is expected that these procedures will be useful for growing and purifying PA, including natural or recombinant PA, as well as various modified or truncated forms of PA, from other microorganisms, particularly other *Bacillus* species and strains. *Bacillus* strains and/or expression systems which are expected to be suitable include, for example, the *B. anthracis* strain described in U.S. Pat. No. 5,840,312 (Nov. 24, 1998) and the *B. subtilis* strain and PA expression system described in U.S. Pat. No. 6,267,966 (Jul. 31, 2001).

In one aspect of the invention, the culture is preferably maintained at about pH 7 to about pH 8, most preferably about pH 7.5, substantially throughout the fermentation process. It has also been found to be advantageous to add EDTA before separating the culture supernatant from the cells, preferably at or near the end of fermentation, since if it is added during the fermentation stage, it may interfere somewhat with the growth of the cells.

The purification procedure of the invention is preferably essentially a three-step procedure, including (1) hydrophobic interaction chromatography, (2) ion exchange chromatography and (3) gel filtration. While ion exchange chromatography may precede hydrophobic interaction chromatography in the purification process, and still permit obtaining a good yield of PA, it is a less efficient process. Therefore, in view of this, it is preferred that hydrophobic interaction chromatography precede ion exchange chromatography in the purification process. Alternatively, this three-step procedure need not be used and an alternative purification scheme may be used.

In addition, the resins used in the exemplified purification procedure can be substituted. For example, in the hydrophobic interaction chromatography step, phenyl sepharose (Pharmacia) is used as the resin in the example, but any other hydrophobic resin can be used. Likewise, in the ion exchange chromatography step, Q sepharose (Pharmacia) is used as the resin in the example, but any other anion exchanger can be used. Likewise, for the gel filtration step, Superdex (Pharmacia) is the residue used in the example, but it can be replaced by other gel filtration resins. Furthermore, with respect to the fermentation conditions, similar compounds can replace the tryptone and the yeast extract that are obtained from Difco.

In other detailed aspects of the invention, novel methods and materials are provided for producing and selecting genetically defined, non-reverting sporulation-deficient mutants of a sporulating bacterium. Exemplary bacteria for which these methods are well suited include *Bacillus anthracis*, *B. thuringiensis*, and *B. cereus*. The sporulation deficient mutants obtained according to the methods of the invention are useful, for example, as hosts for expressing recombinant proteins, including recombinant PA, lethal factor, edema factor, and mutant versions of these proteins, contemplated as components of improved anthrax vaccines.

*Bacillus anthracis* efficiently secretes anthrax toxin proteins, and this feature has been employed herein to develop systems for expressing large amounts of recombinant anthrax toxin proteins, for example up to 100 mg per liter of culture. One disadvantage of *B. anthracis* strains, even those which are avirulent due to removal of the two large virulence plasmids, pXO1 and pXO2, is the formation of very stable spores. This presents certain challenges to the use of these strains for commercial vaccine production.

Development of the BH445 sporulation-deficient strain, as described above, ameliorates this problem. However, there remains a need for yet additional modified strains to further enhance stability of by minimizing the potential for reversion to a sporulation-competent parental phenotype. This may occur, for example, if the selective antibiotic chloramphenicol is not present at effective concentrations.

As used herein, "sporulation-deficient" refers to a mutant bacterial strain that exhibits a significant reduction in sporulation potential as compared to the fully sporulation competent, wild type (wt) counterpart strain. The term sporulation-deficient thus refers to sporulation-incompetent mutants, as well as substantially sporulation-impaired mutants.

The current invention provides for the generation and selection of sporulation-deficient mutants of sporulating bacterial based on growth behavior and morphological appearance. In exemplary embodiments, *B. anthracis* is plated on a suitable, solid growth medium, for example LB agar in plates. Following plating the bacteria are allowed to grow for a suitable period to yield moderate to thick growth on the solid medium. Typically, the growth period is between about 24 hours and 72 hours, more typically between about 36 hours and 48 hours.

In areas of thick growth, parental bacteria are induced by nutrient deprivation to initiate sporulation and cease normal growth. This is because moderate to heavy growth is attended by progressive nutrient depletion in the culture. Nutrient deprivation stress in turn stimulates sporulation in the culture by sporulation-competent bacteria, which cease normal growth.

Within the methods of the invention, sporulation-deficient mutants are isolated within such nutrient-stressed cultures. Within areas of thick growth, rare, spontaneous sporulation-deficient mutants emerge. These are selected based on one or more selection criteria. In particular, the mutants may be isolated by picking from a central area of the culture colonies where nutrient deprivation is increased. Alternatively, the mutants can be selected by picking so-called "cancerous tumors" within in the colonies identified as nodules of protruding bacterial growth on a relatively smooth growth background. In addition, or alternatively, sporulation-incompetent and sporulation-impaired mutants can be selected based on other morphological characteristics exhibited by the mutants under nutrient-stress conditions, for example color and "wetness." Sporulation-deficient mutants of *B. anthracis* are generally whiter in appearance and less "wet" (i.e., glossy or reflective) in comparison to wt.

To further enrich for sporulation mutants according to the foregoing method, bacteria selected as above (e.g., picked from central areas of thick growth) can be grown up in an optional, liquid culture step and re-plated for single colonies. As noted in the examples below, this enrichment yields a large number of candidate mutants. In more detailed embodiments, the methods of the invention can produce plates on which between from 1-10%, 10-25%, 30-50% or more of the colonies exhibit distinct morphology from that of the parental strain.

Unlike previous reports, the current mutant selection procedure does not require the incorporation of dyes (e.g., Congo Red, Aram Cresol Green, and Evans Blue) in the solid culture medium to identify sporulation-deficient variants. Although these dyes may facilitate selection in certain embodiments, the methods of the invention can be practice using a dye-free culture medium. As used herein, "dye free" means that the culture medium is substantially free of any added indicator dyes such that differential staining of mutant and wild type colonies by the indicator dye cannot be visually detected.

The methods of the invention yield sporulation-deficient variants of *B. anthracis* and other sporulating species and strains of bacteria, which are often sporulation-incompetent. Typically, the subject mutants are highly stable by virtue of having deletions in genes required for the production of spores. Strains in which these genes have partial or complete deletions will not revert to sporulation-competence forms at a detectable frequency, and are therefore highly desired for use in vaccine production.

Within exemplary embodiments of the foregoing methods, sporulation-deficient mutants were obtained from three different parental strains of *B. anthracis*: Ames plasmid-free, UM44-1C9, and BH441. These sporulation-deficient strains are useful for the expression of proteins, including recombinant PA, lethal factor, edema factor, and mutant versions of these proteins, contemplated as components of improved anthrax vaccines within the methods and compositions of the invention. Useful candidate strains mutated in particular genes required for sporulation will support higher levels of protein expression, for example from the pYS5-type plasmids typically used for expression.

Within additional aspects of the invention, the expression and stability of two recombinant PA variants, PA-SNKE-ΔFF-E308D (SEQ ID NO: 4) and PA-N657A (SEQ ID NO: 5), were studied. Related methods are provided for producing and recovering native PA; PA wherein the receptor-binding domain has been altered; PA which cannot be cleaved at the chymotrypsin cleavage site; PA which cannot be cleaved at the furin cleavage site; other PA which cannot be cleaved at either the chymotrypsin or the furin cleavage site in addition to the one exemplified herein (see, e.g., those described in (22)); PA fragments (e.g., a PA fragment having aa 175-764 (36)); PA mutants having a strong dominant-negative effect (e.g., PA double mutants K397D and D425K) (37), and PA mutants with substitutions in domain 2 (37)).

Considering the nature of the current anthrax (AVA) vaccine and the adverse events that have been associated with its administration, there is an urgent need for new, recombinant PA (rPA) molecules for use in second generation vaccine development. PA is an essential component of an effective anthrax vaccine. One problem with producing a rPA for vaccine use is that PA is sensitive to proteolytic cleavage at two locations. One target location for cleavage is the furin-cleavage loop, which contains the sequence ArgLysLysArg (residues 164-167 of the mature protein). Cleavage at this site activates PA, exposing the surface at which the two other toxin components bind. Removal of the furin loop will prevent intoxication mediated by the other toxin components. The second cleavage loop (residues 304-319) contains the sequence PhePheAsp (residues 313-315), making PA sensitive to cleavage by chymotrypsin and thermolysin.

One strategy for removing this cleavage site involves deleting Phe313 and Phe314. While deletion of these two Phe residues prevents cleavage by chymotrypsin and thermolysin, preparations of this form of rPA still exhibit degradation products indicative of cleavage in the loop, presumably by a different protease.

In related aspects of the invention, one or more contiguous amino acid residues are deleted or substituted in a "flexible", exposed, or loop segment of a recombinant PA protein. Flexible, exposed, and loop segments of PA are identified by X-ray crystallography and other structural analytic methods known in the art. In this context, target segments of PA for mutagenesis include residues not seen in the crystal structure of PA, including cleavage loop segments identified as residues 162-174, residues 304-319, and other exposed or flexible segments including residues 1-13, 99-102, and 512-515 (see FIGS. 7 and 8). All of these segments are useful targets for mutation within the invention to yield a rPA having improved characteristics for vaccine development, including enhanced resistance to protolytic degradation.

Within the foregoing targeted segments of PA, one or more amino acids will be deleted or modified (e.g., by chemical modification or substitution with another amino acid), and typically the deletion or modification will reduce susceptibility of the rPA to proteolytic degradation (e.g., by removing a cleavage target site or altering an amino acid side chain to interfere with a cleavage interaction that would target the native PA protein). Typically, 1-15 amino acids will be deleted, often in combination with substitution of one or more amino acid(s) within the targeted PA segment. In other embodiments, the number of contiguous amino acids deleted from the target segment encompasses 3-12, 4-10, 5-8, or 6-7 residues.

In one exemplary embodiment, the invention provides a stable, recombinant PA molecule having a deletion of exemplary segments from both the chymotrypsin-sensitive loop and the furin-cleavage loop. This novel rPA double deletion mutant described here has both cleavage-sensitive loops removed to create a more stable, inactive, PA mutant protein suitable for vaccine production. This double mutant modification was accomplished by: (a) deletion of residues 162 through 167 and the substitution of Ile for Ser at residue 168; (b) the deletion of residues 304-317 and the substitution of Gly for Set at residue 319 (see FIGS. 7 and 8). The changes made in (a) remove the furin-cleavage loop, while the changes in (b) substitute two Gly residues for the entire chymotrypsin-cleavage loop (FIG. 8). This and other mutant rPAs produced according to the invention exhibit significantly increased stability compared to wt PA. In particular, the stability of selected mutant rPAs according to the invention to proteolytic degradation will be increased by at least 15%, often 20-30%, 50%, 75%, up to 100%, 200% or more compared to stability of wt PA under comparable conditions.

In a related aspect of the invention, polynucleotides and expression vectors encoding a double deletion mutant form of rPA are provided. One such exemplary polynucleotide is shown in FIGS. 9A and 9B. Also provided are host cells incorporating an expression vector operable to direct expression of a mutant rPA of the invention within the host cell.

In additional aspects of the invention, the methods herein are useful for producing and recovering PA in which the chymotrypsin site, FF, is replaced by a furin site. This may be a suicide protein, getting easily cleaved by furin after binding to receptor. Cleavage at that site inactivates PA.

The methods of the invention are also useful for producing and recovering PA with a protease cleavage site (thrombin, Factor IV, etc.) at approximately residue 605. PA made in large amounts in the expression system could be cleaved to produce a soluble domain 4, which would compete with PA for receptor, and could be a therapeutic agent.

The methods of the invention are also useful for producing and recovering PA with matrix metalloprotease or plasminogen activator sites replacing the furin site (38, 39).

The methods of the invention are also useful for producing and recovering other proteins, such as LF. See, e.g., (21), wherein expression system is the same, except the structural gene for PA is replaced by the LF gene. This can be generalized to include LF mutants altered in the catalytic site residues: HEFGH, 686-690. The system may also have utility with EF.

The following examples are provided by way of illustration, not limitation.

EXAMPLE 1

In this example, the expression and the stability of two recombinant PA variants, PA-SNKE-ΔFF-E308D (SEQ ID NO: 4) and PA-N657A (SEQ ID NO: 5), were studied. These proteins were expressed in the non-sporogenic avirulent strain BH445. Initial results indicated that PA-SNKE-ΔFF-E308D (SEQ ID NO: 4), which lacks two proteolysis-sensitive sites, is more stable than PA-N657A (SEQ ID NO: 5). Process development was conducted to establish an efficient production and purification process for PA-SNKE-ΔFF-E308D (SEQ ID NO: 4). Various parameters such as pH, media composition, growth strategy, and protease inhibitors composition were analyzed. The production process chosen was based on batch growth of B. anthracis using tryptone and yeast extract as the only sources of carbon, pH control at 7.5, and antifoam 289. Optimal harvest time was found to be 14-18 hours after inoculation, and EDTA (5 mM) was added upon harvesting for proteolysis control. In one of the processes described herein, recovery of the PA was performed by expanded bed adsorption (EBA) on a hydrophobic interaction resin, eliminating the need for centrifugation, microfiltration, and diafiltration. The EBA step was followed by ion exchange and gel filtration. PA yields before and after purification were 130 mg/L and 90 mg/L, respectively.

Materials and Methods

Strains and Plasmids

The non-sporogenic, protease deficient, avirulent strain *B. anthracis* BH445 (pXO1−, pXO2−, cm^r) was used (17). The *Bacillus-E. coli* shuttle vector pYS5 (amp^r, kan^r) (26) was used to clone two recombinant forms of the protective antigen: N657A and SNKE-ΔFF-E308D (SEQ ID NO: 4) (28). In the N657A mutant (SEQ ID NO: 5), the receptor-binding domain of PA was altered by substitution of Asn with Ala at position 657 (domain 4). In the SNKE-ΔFF-E308D (SEQ ID NO: 4) mutant two regions were altered, the furin site (RKKR$^{167}$ to SNKE$^{167}$) and the chymotrypsin site (two Phe at positions 313-314 were deleted and Glu acid at position 308 was substituted with Asp). Both PA constructs contain the DNA sequence encoding the signal peptide of PA.

Culture and Expression Conditions

Modified FA medium (21) containing (per liter) 35 g tryptone (Difco Laboratories, Detroit, Mich.), 5 g yeast extract (Difco Laboratories), and 100 mL of 10× salts was used in all experiments. The 10× salt solution (per liter) consisted of 60 g $Na_2HPO_4 \cdot 7H_2O$, 10 g $KH_2PO_4$, 55 g NaCl, 0.4 g L-tryptophan, 0.4 g L-methionine, 0.05 g thiamine, and 0.25 g uracil. It was filter-sterilized and added to the fermentor after cooling. The pH of the medium was adjusted to 7.5; 100 μg/mL kanamycin and 20 μg/mL chloramphenicol were added. Fermentation experiments were performed by inoculating a 12-14 hour-old starter culture grown from a frozen stock. The medium in the fermentor was supplemented with 0.2 mL/L of antifoam 289 (Sigma, St. Louis, Mo.). Three- to ten-liter fermentations were done using B. Braun Biostat MD DCU (Melsungen, Germany), controlling dissolved oxygen (DO) at 30% saturation, temperature at 37° C., and pH at 7.5 with HCl and $NH_4OH$. At harvest time, 5 mM EDTA and 10 μg/mL PMSF (phenylmethyl sulfonyl fluoride) (in one of the experiments described herein) were added to the culture. Shake flask experiments (100 mL) utilizing modified FA medium were supplemented with glucose, lactose, glycerol, and casitone at a concentration of 10 g/L.

Analytical Methods

Optical density (OD) was measured at 600 nm. Protease analysis was done on supernatant samples collected during growth and stored frozen at −20° C. EDTA was added to supernatant samples used for SDS-PAGE and radial immunodiffusion to a final concentration of 10 mM.

Extracellular protease activity was detected using the EnzChek green fluorescence assay kit (Molecular Probes, Eugene, Oreg.). Fluorescence was measured with a LS50B luminescence spectrophotometer (Perkin-Elmer, Boston, Mass.). This assay was conducted at pH of 7.5 or 6.0 depending on the experiment. Proteolytic activity is reported as fluorescence change per unit sample.

Protein was determined using BCA assay (Pierce, Rockford, Ill.). PA expression was quantified by SDS-PAGE (Invitrogen/Novex, Carlsbad, Calif.) gel analysis and by the Mancini immunodiffusion assay (19) using agarose plates containing polyclonal PA antibody. Pure PA was used as the standard, both polycolonal PA antibodies and pure PA were supplied by Dr. Stephen Leppla.

Purification a. Packed Bed Hydrophobic Interaction Chromatography

The cell suspension containing 5 mM EDTA was centrifuged and the supernatant passed through a 0.2 μm hollow fiber filter (AGT, Needham, Mass.). The filtered broth was then concentrated 20× using a 10K membrane in a Pellicon-2 (Millipore, Bedford, Mass.). 200 g $(NH_4)_2SO_4$ per liter (1.5 M) were added to the concentrated supernatant. The small amount of precipitate produced after addition of $(NH_4)_2SO_4$ was eliminated with centrifugation and filtration. Phenyl Sepharose Fast Flow (Amersham Pharmacia Biotech) was equilibrated with buffer containing 1.5 M $(NH_4)_2SO_4$/10 mM HEPES/5 mM EDTA pH=7.0 (equilibration buffer) at a flow rate of 15 cm/h. After sample loading, the column was washed with 10 column volumes (CV) of equilibration buffer and PA was eluted with a 30 CV linear gradient from 1.5 M to 0 M $(NH_4)_2SO_4$ in 10 mM HEPES/5 mM EDTA; pH=7.0. Fractions were analyzed by SDS-PAGE and the PA-containing samples were pooled for further purification.

b. Expanded Bed Hydrophobic Interaction Chromatography

The cell suspension containing 5 mM EDTA was diluted 1:1 with buffer containing 3.0 M $(NH_4)_2SO_4$/20 mM HEPES/5 mM EDTA and 0.005% Pluronic F-68 (Life Technologies, Inc. Gaithersburg, Md.). STREAMLINE™ Phenyl adsorbent, (Amersham Pharmacia Biotech) was expanded in a streamline column in equilibration buffer. The diluted cell suspension was loaded upward at 300 cm/h. The column was washed in expanded mode (2) with 10 CV of equilibration buffer containing 0.005% pluronic F-68. Elution was performed in packed bed mode with 8 CV of elution buffer at 100 cm/h. The eluent was analyzed by SDS-PAGE and radial immunodifussion.

c. Anion Exchange Chromatography

Fractions from HIC were dialyzed against 20 mM Tris pH=8.9 and loaded on a Q Sepharose Fast Flow (Amersham Pharmacia Biotech) column equilibrated with 20 mM Tris pH=8.9 at 15 cm/h. The protein was eluted using a 20 CV linear gradient from 0 to 0.5 M NaCl in the same buffer. PA containing fractions were concentrated and dialyzed against PBS.

d. Gel Filtration

The pooled PA was further purified using a Superdex 75 column (Amersham Pharmacia Biotech) in PBS/5 mM EDTA pH=7.4 at 12 cm/h.

Figure 1A:
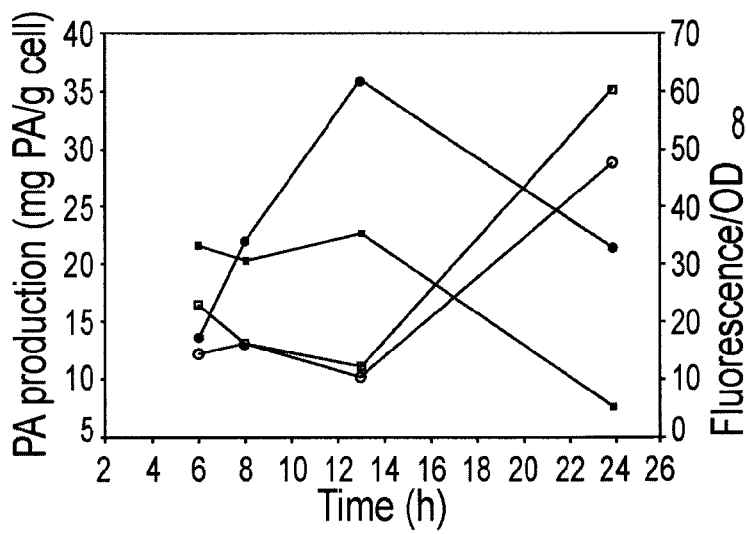
FIG. 1. Production and proteolytic activity of PA-SNKE-ΔFF-E308D (SEQ ID NO: 4) and PA-N657A (SEQ ID NO.
Figure 1B:
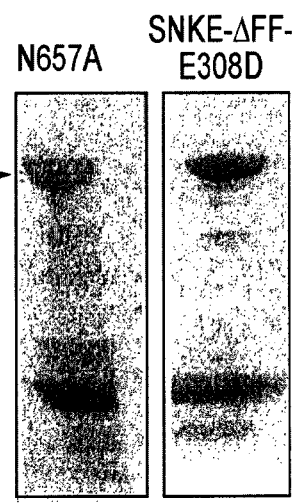

Results and Discussion a. Expression of Two Recombinant PAs:
PA-N657A and PA-SNKE-ΔFF-E308D The expression of two recombinant versions of PA and the extracellular proteolytic activity of the culture were analyzed (FIG. 1). Production of PA-SNKE-ΔFF-E308D (SEQ ID NO: 4), the protein lacking the furin and chymotrypsin cleavage sites, was nearly 60% higher than that of PA-N657A (SEQ ID NO: 5), the protein containing a mutation in the receptor-binding domain (FIG. 1a). The extracellular proteolytic activity (fluorescence/OD) of both cultures was similar. SDS-PAGE analysis of partially purified PA recovered from these cultures shows higher concentration of smaller fragments in the sample from PA-N657A (SEQ ID NO: 5) compared to the sample from PA-SNKE-ΔFF-E308D (FIG. 1b; SEQ ID NO: 4). Western blot analysis with polyclonal PA antibody confirmed that the smaller fragments were reactive against PA (data not shown). As indicated in FIG. 1a, the proteolytic activity was similar in both strains. Therefore, it was apparent that PA-SNKE-ΔFF-E308D (SEQ ID NO: 4) is a better candidate, due to its stability, and it was selected for further studies.

b. pH Effect

Based on previous information (5, 21), initial production studies with PA-SNKE-ΔFF-E308D (SEQ ID NO: 4) were done by controlling pH with NH$_4$OH only, which resulted in pH 8.7 at the end of the fermentation. When pH was controlled at 7.4 during the entire fermentation, the PA production was 30 mg per g cell and the proteolytic activity per OD unit was 8, compared to values of 20 mg PA per g cells and proteolytic activity per OD of 30 when the pH control was done only by NH$_4$OH. When the process was performed at a lower pH, both PA production and protease activity were lower. At pH 6.1 production declined nearly six times and protease activity two times compared to what was found at pH 7.4. Possibly, intracellular expression is lower or secretion is inhibited at low pH. From the above information it is obvious that pH significantly affects the proteolytic activity and the PA expression. Controlling pH throughout the fermentation process resulted in a 30% increase in PA yield, compared to previously reported strategies.

c. Effect of Various Carbon Sources and Protease Inhibitors

Attempts to increase PA expression by supplementing the basic growth medium with different carbon sources is summarized in Table 1.

TABLE 1

Effect of various carbon sources on PA production.

| Medium | PA production | |
|---|---|---|
| | mg PA/g cell | mg PA/L culture |
| Basic medium | 31.3 | 129.5 |
| Glycerol + basic medium | 23.7 | 117.3 |
| Glucose + basic medium | 25.3 | 113.3 |
| Lactose + basic medium | 33.9 | 116.0 |
| Casitone + basic medium | 28.3 | 135.1 |

Neither the volumetric production nor the production per gram cells could be enhanced with the addition of various carbon sources. The effect of PMSF and EDTA on extracellular proteolysis was also examined. As shown in FIG. 2, addition of EDTA (15 mM) significantly reduced proteolytic activity whereas the proteolytic activity of the PMSF-containing fraction (1 g/mL) was similar to that of the control. Based on this information, EDTA was added at the end of the fermentation, before the protein was processed.

d. Growth and Production Conditions

Based on the parameters determined previously, a production process for the recombinant PA-SNKE-ΔFF-E308D (SEQ ID NO: 4) from *B. anthracis* BH445 was established. The process is based on growth in a batch fermentation controlled at pH 7.5 with NH$_4$OH/HCl and at 30% dissolved oxygen saturation for a period of 18 hours. A typical fermentation is seen in FIG. 3.

In general, the final OD$_{600}$ values fluctuated between 16 to 20. During the first five hours, growth was exponential and the pH was controlled by base addition. Later in the fermentation the pH was controlled by acid addition. Accumulation of PA occurred mostly during the stationary phase and reached a final concentration of 160 mg per liter. The results shown in FIG. 4 indicate that PA degraded if the fermentation was extended for more than 18 hours, therefore, a harvest time between 14 and 18 hours was selected.

Attempts to increase the PA production by implementing a fed-batch growth strategy were conducted. The addition of 10× tryptone/yeast extract/salts or 50% glucose/10× salts resulted in a 50% increase in cell density but not an increase in protein production (FIG. 5). The observations that PA production was not improved by the implementation of a fed batch growth strategy or by the addition of various carbon sources such as casein, glucose, glycerol or lactose is an indication that perhaps a specific nutritional factor is missing. It is also important to mention that the specific proteolytic activity was almost five times lower when glucose was added to the tryptone/yeast extract media (FIG. 6). This was expected since glucose is known to be a repressor of proteases in *Bacillus* (10, 25).

e. Purification

The purification protocol developed for PA (Materials and Methods) consisted of hydrophobic interaction chromatography (Phenyl Sepharose) followed by anion exchange (Q Sepharose) and gel filtration (Superdex 75).

Replacing the initial capturing step with expanded bed chromatography (2) can simplify and shorten the recovery process since it eliminates the clarification steps. Therefore, the use of expanded bed adsorption (EBA) was investigated by substituting the traditional packed-bed resin (Phenyl Sepharose) with the expanded bed hydrophobic resin STREAMLINE™ Phenyl adsorbent. The static binding capacity for STREAMLINE™ Phenyl adsorbent was approximately 15 mg protein/mL of resin, which is comparable to the capacity of Phenyl Sepharose. Optimal binding of PA to STREAMLINE™ Phenyl adsorbent occurred at 1.5 M (NH$_4$)$_2$SO$_4$.

Preliminary experiments performed with cell-containing broth in expanded mode resulted in the formation of aggregates and eventual collapse of the bed. It was possible to stabilize the expanded column only after the addition of a detergent which probably altered some of the hydrophobic interactions but did not prevent PA from binding. Pluronic F-68 was chosen due its non-toxicity in humans. The static binding capacities of STREAMLINE™ Phenyl adsorbent were 15, 11, and 5 mg protein/mL resin with 0%, 0.005%, and 0.01% pluronic F-68, respectively. Successful operation of the HIC EBA column occurred when using a load concentration of 15 g wet cells/L, 0.8 mL resin/g wet cells, and 0.005% pluronic F-68 in the load as well as the wash buffer. Under these conditions some signs of aggregation appeared at the end of the loading phase but cell debris was eliminated in the washing phase. A 70% recovery was obtained.

PA purity after hydrophobic interaction chromatography was higher than 80%. Further purification was achieved by adding gel filtration step (FIG. 6, Lane b). However, this material was not stable when stored at 4° C. for three months (FIG. 6, Lane c). In contrast, pure and stable PA was obtained after hydrophobic interaction chromatography on expanded bed, followed by anion exchange and gel filtration (FIG. 6, Lane d). Similar results to the expanded bed process were obtained when packed bed hydrophobic interaction chromatography was followed by ion exchange and gel filtration (FIG. 6, Lane a).

Replacing the packed-bed capturing step with expanded bed adsorption proved to be more efficient since it eliminated the centrifugation and filtration steps, however, twenty times more (NH$_4$)$_2$SO$_4$ and three times more resin were required to process the same amount of culture (Table 2).

TABLE 2

Comparison of packed bed and expanded bed absorption as capturing processes for PA

| Packed Bed | Expanded Bed Adsorption |
|---|---|
| 1. Total processing time 15.5 h<br>  a) downstream processing:<br>    6 h (4 unit operations)<br>  b) loading: 2 h<br>  c) column wash: 3.5 h<br>  d) elution: 4 h | 1. Total processing time: 8 h<br>  a) downstream processing:<br>    1 h (1 unit operation)<br>  b) loading: 4 h<br>  c) column wash: 1.5 h<br>  d) elution: 1.5 h |
| 2. 400 g $(NH_4)_2SO_4$ needed | 2. 8000 g $(NH_4)_2SO_4$ needed |
| 3. 100 mL resin needed | 3. 300 mL resin needed |
| 4. Load/wash steps require little attention | 4. Load/wash steps cannot be left unattended |
| 5. 82% recovery | 5. 70% recovery |

Initial work with hydrophobic interaction chromatography using expanded bed ad sorption to capture PA resulted in bed collapse. This was avoided after the addition of a surfactant (pluronic F-68). These results suggest that the characteristics of the cell membrane were most likely the cause of cell aggregation. Since no polyglutamic acid capsule is present in the recombinant strain, the two hydrophobic membrane proteins forming the S-layer (4, 6) may be responsible for associating with neighboring cell membranes and the resin. After evaluating the possible interactions affecting the system, it was found that successful operation of the expanded bed was possible by carefully adjusting the cell concentration of the load, increasing the adsorbent-to-cell ratio, and choosing the appropriate detergent type and concentration. The expanded bed approach was more efficient in spite of the slightly lower yield (70% vs. 82%) and the higher amount of $(NH_4)_2SO_4$ and resin needed since it eliminated the need for centrifugation and filtration. To obtain stable and highly purified protein, anion exchange and gel filtration steps were added.

CONCLUSIONS

Once the gene encoding PA (pagA) was cloned (31) and sequenced (32), several researchers have reported on the expression of PA in hosts like *B. subtilis* (1, 13, 20, 26), *E. coli* (8, 24, 31), *Salmonella typhimurium* (3), viruses (11), and avirulant *B. anthracis* (5, 15). From these reports, the highest PA yield achieved has been in the order of 50 mg/L in *B. anthracis* (15). In this work, a scalable fermentation and purification process suitable for vaccine development which produced almost three times more product than what has been reported earlier, is presented. This was accomplished by using a biologically inactive protease-resistant PA variant in a protease-deficient nonsporogenic avirulent strain of *B. anthracis*.

EXAMPLE 2

Composition of the Vaccines

Four combinations of the recombinant (modified) protective antigen ("rPA") were made: (1) rPA in PBS ("phosphate buffered saline"), (2) rPA in formalin, (3) rPA in aluminum hydroxide and (4) rPA in formalin and aluminum hydroxide. Another formulation of succinylated rPA was prepared and tested (data not shown).

EXAMPLE 3

Immunogenicity in Mice

The four formulations described above were immunogenic in mice, and induced antibody levels comparable to those induced by the currently licensed anthrax vaccine. The induced antibodies had anthrax toxin neutralizing activity. It is planned to evaluate these formulations in humans, and to choose the best one for use as a vaccine.

The data from the mice experiments are set forth in the tables 3 to 5 below:

TABLE 3

Number of Mice and Immunogen

| Group Number | Number of Mice | Immunogen |
|---|---|---|
| 1056 | 11 | PA (2.5 µg)-Untreated |
| 1057 | 11 | PA (12.5 µg)-Untreated |
| 1058 | 11 | PA (2.5 µg) + Alum |
| 1059 | 10 | PA $_{SUCC}$ 10:1.25 (2.5 µg) |
| 1060 | 10 | PA $_{SUCC}$ 10:1.25 (12.5 µg) |
| 1061 | 10 | PA $_{SUCC}$ 10:3 (2.5 µg) |
| 1062 | 10 | PA $_{SUCC}$ 10:3 (12.5 µg) |
| 1063 | 10 | PA-Formalin 0.3 (2.5 µg) |
| 1064 | 10 | PA-Formalin 0.3 (12.5 µg) |
| 1065 | 10 | PA-Formalin 3.0 (2.5 µg) |
| 1066 | 10 | PA-Formalin 3.0 (12.5 µg) |
| 1067 | 10 | PA-Formalin 7.12 (2.5 µg) |
| 1068 | 10 | PA-Formalin 7.12 (12.5 µg) |
| 1069 | 11 | Anthrax Vaccine 0.1 ml |
| 1070 | 10 | Control |

TABLE 4

Antibody Levels and Neutralization Titers

| Mice | µg/ml | Neutral, Titer |
|---|---|---|
| 1056A | 130.64 | 4000 |
| 1056B | 11.24 | 200 |
| 1056K | 21.3 | 1000 |
| 1057A | 146.65 | 3000 |
| 1057I | 490.14 | 7000 |
| 1058A | 725.31 | 8000 |
| E | 710.46 | 7000 |
| J | 513.46 | 4000 |
| 1059A | 53.89 | 1500 |
| 1060A | 125.92 | 850 |
| 1061A | 97.1 | 1500 |
| C | 21.2 | 200 |
| E | 54.22 | 700 |
| 1062A | 24.9 | 1500 |
| J | 14.35 | 2000 |
| 1063A | 68.31 | 1500 |
| C | 179.16 | 2000 |
| H | 564.94 | 2000 |
| 1064A | 581.34 | 10,000 |
| 1064D | 204.56 | 8000 |
| E | 742.21 | 11,000 |
| F | 418.95 | 7000 |
| G | 814.91 | 10,000 |
| 1065A | 77.73 | 1250 |
| E | 214.37 | 5000 |
| 1066C | 65.47 | 4000 |
| D | 513.32 | 10,000 |
| E | 248.91 | 4000 |
| F | 260.36 | 8000 |
| J | 1041.65 | 10,000 |
| 1067A | 261.54 | 3000 |
| G | 415 | 5000 |
| 1068A | 512.99 | 10,000 |
| I | 414.82 | 5000 |
| 1069A | 339.18 | 3000 |
| 1069J | 879.65 | 3000 |
| 1070E | <.05 | 20 |

5-6 weeks old female general purpose mice were injected subcutaneously with 0.1 mL of the immunogens depicted in Table 3, 2 or 3 times 2 weeks apart. The mice were exsanguinated one week after the last injection and their sera assayed for IgG anti PA and anthrax toxin neutralization. Antibodies measured by Elisa were related to a standard containing 1.8 mg/ml of anti-PA monoclonal antibody.

TABLE 5

IgG anti PA levels induced in mice by various rPA formulations

| PA lot | formulation | dose × number of injections | µg/ml |
|---|---|---|---|
| 0 | PA | 2.5 µ × 2 | 1.3 |
| 0 | PA | 2.5 µ × 3 | 109.1 |
| 2 | PA | 2.5 µ × 3 | 24.9 |
| 2 | PA | 12.5 µ × 3 | 226 |
| 0 | PA/Al (OH)$_3$ | 2.5 µ × 2 | 86.1 |
| 0 | PA/Al (OH)$_3$ | 2.5 µ × 3 | 312. |
| 2 | PA/Al (OH)$_3$ | 2.5 µ × 3 | 435. |
| 2 | PA formalin 0.3 | 2.5 µ × 3 | 182 |
| 2 | PA formalin 0.3 | 12.5 µ × 3 | 350. |
| 0 | PA formalin 3.0 | 2.5 µ × 2 | 2.79 |
| 0 | PA formalin 3.0 | 2.5 µ × 3 | 136.4 |
| 0 | PA formalin 3.0 | 5.0 µ × 2 | 1.98 |
| 2 | PA formalin 3.0 | 2.5 µ × 3 | 220 |
| 2 | PA formalin 3.0 | 12.5 µ × 3 | 270 |
| 0 | PA formalin 7.12 | 2.5 µ × 3 | 266 |
| 0 | PA formalin 7.12 | 12.5 µ × 3 | 229 |
| Anthrax Vaccine | | 1/10 human dose × 2 | 43.15 |
| | | 1/10 human dose × 3 | 297 |
| PBS control | | ×2 | <.05 |
| | | ×3 | <.05 |

5-6 weeks old female mice, 10 per group, were injected subcutaneously with the listed formulations, 2 or 3 times, two weeks apart and exsanguinated one week after the last injection. Antibodies were measured by Elisa, calculated relative to a standard containing 1.8 mg/ml of anti-PA monoclonal antibody, and expressed as geometric means of the groups.

EXAMPLE 4

The present example describes novel methods and materials for production of genetically defined, non-reverting sporulation-deficient mutants of *Bacillus anthracis* for use as a host for expression of recombinant proteins. Through analysis of the growth behavior and morphological appearance of *B. anthracis* growing on certain solid media (e.g., LB agar plates), it was discovered that in areas of thick growth, parental bacteria are induced by nutrient deprivation to initiate sporulation and cease normal growth.

Briefly, inocula of *B. anthracis* were plated on LB agar plates and cultured for approximately 36-48 hrs to yield moderate to heavy growth. In areas of thick growth rare, spontaneous sporulation-deficient mutants emerged that were then identified and isolated. The sporulation-deficient mutants were successfully isolated by picking from central portions of the culture colonies where nutrient deprivation is presumptively increased. Additional mutant isolates were obtained by picking cancerous tumors that appeared as nodules of protruding bacterial growth on a relatively smooth growth background. Mutant selection was also achieved by observation of alternative morphological characteristics exhibited by sporulation-incompetent and sporulation-impaired mutants, including increased whiteness of color and decreased wetness compared to wt.

To further enrich for sporulation mutants, bacteria selected as above were grown up in liquid culture and re-plated for single colonies. This enrichment routinely produced plates on which 1-50% of the colonies exhibit distinct morphology from that of the parental strain. The morphological variants, when purified and tested, were almost always found to be unable to produce spores. Analysis of many such mutants by PCR demonstrates that the subject mutants have deletions in genes known to be required for the production of spores. Strains in which these genes have deletions will not revert to sporulation-competence forms at a detectable frequency, and are therefore highly desired for use in vaccine production.

To illustrate the broad applicability of the foregoing mutant selection protocols, sporulation-deficient mutants were obtained from three different parental strains: Ames plasmid-free, UM44-1C9, and BH441. Accordingly, a large collection of mutant strains can be generated and selected following the disclosure herein.

EXAMPLE 5

The present example describes the creation of a novel, stable, recombinant PA molecule by deletion of exemplary segments of both the chymotrypsin-sensitive loop and the furin-cleavage loop. Considering the nature of the current anthrax (AVA) vaccine and the adverse events that have been associated with its administration, second generation vaccines there is an urgent need for new, recombinant PA (rPA) molecules for use in vaccine development. PA is an essential component of an effective anthrax vaccine. One problem with producing a rPA for vaccine use is that PA is sensitive to proteolytic cleavage at two locations. One target location for cleavage is the furin-cleavage loop, which contains the sequence ArgLysLysArg (residues 164-167 of the mature protein). Cleavage at this site activates PA, exposing the surface at which the two other toxin components bind. Removal of the furin loop will prevent intoxication mediated by the other toxin components. The second cleavage loop (residues 304-319) contains the sequence PhePheAsp (residues 313-315), making PA sensitive to cleavage by chymotrypsin and thermolysin. As described above, one strategy for removing this cleavage site involves deleting Phe313 and Phe314. While deletion of these two Phe residues prevents cleavage by chymotrypsin and thermolysin, preparations of this form of rPA still exhibit degradation products indicative of cleavage in the loop, presumably by a different protease.

The novel rPA described in the present example has both cleavage-sensitive loops removed to create a more stable, inactive, PA mutant protein suitable for vaccine production. This double mutant modification was accomplished by: (a) deletion of residues 162 through 167 and the substitution of Ile for Ser at residue 168; (b) the deletion of residues 304-317 and the substitution of Gly for Ser at residue 319 (see FIGS. 7 and 8). The changes made in (a) remove the furin-cleavage loop, while the changes in (b) substitute two Gly residues for the entire chymotrypsin-cleavage loop (FIG. 8). An exemplary polynucleotide encoding this rPA is shown in FIGS. 9A and 9B.

Expression of the double mutant and comparative expression of wt PA was achieved using a sporulation-incompetent (spo-) anthrax strain as previously described. Supernatant protein samples from the resulting cultures were analyzed on non-reducing polyacrylamide gel electrophoresis (non-reducing PAGE). The bands corresponding to the rPA and wt PA were compared to estimate degradation in the compared samples. In this context, expression levels and secretion efficiency are expected to be similar for the rPA and wt PA samples. The results of this study showed that the double mutant rPA was significantly more stable to enzymatic degradation than the wild-type (wt) PA.

In further detailed studies, both avirulent BH441 and UM44-1C9 parents were plated at high cell density and putative sporulation-deficient mutants selected based on growth retardation and colony morphology as above. A panel of sub-clones from each parent tested was cultured as described above in the absence of selection and using the 48 hr passage interval, designed to enrich for spores. Following heat treatment and plating on agar in the absence of selection, all sub-clones were completely asporogenic with no germination detected. The newly identified BH441 and UM44-1C9 sub-clones are stable in the absence of selection and show no signs of reversion to the wild-type phenotype under growth limiting conditions designed to enrich for revertants. No antibiotic is required to maintain this phenotype.

Although the foregoing invention has been described in detail by way of example for purposes of clarity of understanding, it will be apparent to the artisan that certain changes and modifications may be practiced within the scope of the appended claims which are presented by way of illustration not limitation. In this context, various publications and other references have been cited within the foregoing disclosure for economy of description. Each of these references is incorporated herein by reference in its entirety for all purposes.

What is claimed:

1. A method for inducing serum antibodies that have neutralizing activity for *Bacillus anthracis* (*B. anthracis*) toxin comprising administering to a mammal a pharmaceutical composition comprising an amount of a protein comprising the amino acid sequence of SEQ ID NO: 4 sufficient to elicit production of said antibodies.

2. The method of claim 1 wherein the mammal is a human.

3. The method of claim 1, wherein the protein comprising the amino acid sequence of SEQ ID NO: 4 is produced by culturing a cell or microorganism comprising a nucleotide sequence encoding the protein comprising the amino acid sequence of SEQ ID NO: 4 in a manner to cause expression of SEQ ID NO: 4, wherein the culture medium is maintained at about pH 7 to about pH 8 substantially throughout the fermentation process.

4. The method of claim 3, wherein said protein is recovered using hydrophobic interaction chromatography, ion exchange chromatography and gel filtration.

5. The method of claim 4, wherein EDTA is added to the culture medium prior to the recovery of said protein.

6. The method of claim 3, wherein the microorganism is a *Bacillus*.

7. The method of claim 3, wherein the cell or microorganism is a protease-deficient nonsporogenic avirulent strain of *B. anthracis*.

8. The method of claim 7, wherein the protease-deficient nonsporogenic avirulent strain of *B. anthracis* is BH445.

9. The method of claim 3, wherein the pH is maintained with HCl and NH$_4$OH.

10. The method of claim 3, wherein the pH is maintained at about pH 7.5 throughout the fermentation.

11. The method of claim 1, wherein the pharmaceutical composition further comprises an adjuvant.

12. The method of claim 11, wherein the adjuvant comprises aluminum hydroxide.

13. The method of claim 1, wherein the pharmaceutical composition further comprises formalin.

* * * * *

SEQUENCE LISTING

```
<160> NUMBER OF SEQ ID NOS: 5

<210> SEQ ID NO 1
<211> LENGTH: 715
<212> TYPE: PRT
<213> ORGANISM: Artificial Sequence
<220> FEATURE:
<223> OTHER INFORMATION: Mature double mutant protective antigen

<400> SEQUENCE: 1

Glu Val Lys Gln Glu Asn Arg Leu Leu Asn Glu Ser Glu Ser Ser Ser
1               5                   10                  15

Gln Gly Leu Leu Gly Tyr Tyr Phe Ser Asp Leu Asn Phe Gln Ala Pro
            20                  25                  30

Met Val Val Thr Ser Ser Thr

```
Ser Asn Ser Asn Ser Ser Thr Val Ala Ile Asp His Ser Leu Ser Leu
305                 310                 315                 320
Ala Gly Glu Arg Thr Trp Ala Glu Thr Met Gly Leu Asn Thr Ala Asp
            325                 330                 335
Thr Ala Arg Leu Asn Ala Asn Ile Arg Tyr Val Asn Thr Gly Thr Ala
            340                 345                 350
Pro Ile Tyr Asn Val Leu Pro Thr Thr Ser Leu Val Leu Gly Lys Asn
            355                 360                 365
Gln Thr Leu Ala Thr Ile Lys Ala Lys Glu Asn Gln Leu Ser Gln Ile
370                 375                 380
Leu Ala Pro Asn Asn Tyr Tyr Pro Ser Lys Asn Leu Ala Pro Ile Ala
385                 390                 395                 400
Leu Asn Ala Gln Asp Asp Phe Ser Ser Thr Pro Ile Thr Met Asn Tyr
            405                 410                 415
Asn Gln Phe Leu Glu Leu Glu Lys Thr Lys Gln Leu Arg Leu Asp Thr
            420                 425                 430
Asp Gln Val Tyr Gly Asn Ile Ala Thr Tyr Asn Phe Glu Asn Gly Arg
            435                 440                 445
Val Arg Val Asp Thr Gly Ser Asn Trp Ser Glu Val Leu Pro Gln Ile
450                 455                 460
Gln Glu Thr Thr Ala Arg Ile Ile Phe Asn Gly Lys Asp Leu Asn Leu
465                 470                 475                 480
Val Glu Arg Arg Ile Ala Ala Val Asn Pro Ser Asp Pro Leu Glu Thr
            485                 490                 495
Thr Lys Pro Asp Met Thr Leu Lys Glu Ala Leu Lys Ile Ala Phe Gly
            500                 505                 510
Phe Asn Glu Pro Asn Gly Asn Leu Gln Tyr Gln Gly Lys Asp Ile Thr
            515                 520                 525
Glu Phe Asp Phe Asn Phe Asp Gln Gln Thr Ser Gln Asn Ile Lys Asn
            530                 535                 540
Gln Leu Ala Glu Leu Asn Ala Thr Asn Ile Tyr Thr Val Leu Asp Lys
545                 550                 555                 560
Ile Lys Leu Asn Ala Lys Met Asn Ile Leu Ile Arg Asp Lys Arg Phe
            565                 570                 575
His Tyr Asp Arg Asn Asn Ile Ala Val Gly Ala Asp Glu Ser Val Val
            580                 585                 590
Lys Glu Ala His Arg Glu Val Ile Asn Ser Ser Thr Glu Gly Leu Leu
            595                 600                 605
Leu Asn Ile Asp Lys Asp Ile Arg Lys Ile Leu Ser Gly Tyr Ile Val
            610                 615                 620
Glu Ile Glu Asp Thr Glu Gly Leu Lys Glu Val Ile Asn Asp Arg Tyr
625                 630                 635                 640
Asp Met Leu Asn Ile Ser Ser Leu Arg Gln Asp Gly Lys Thr Phe Ile
            645                 650                 655
Asp Phe Lys Lys Tyr Asn Asp Lys Leu Pro Leu Tyr Ile Ser Asn Pro
            660                 665                 670
Asn Tyr Lys Val Asn Val Tyr Ala Val Thr Lys Glu Asn Thr Ile Ile
            675                 680                 685
Asn Pro Ser Glu Asn Gly Asp Thr Ser Thr Asn Gly Ile Lys Lys Ile
            690                 695                 700
Leu Ile Phe Ser Lys Lys Gly Tyr Glu Ile Gly
705                 710                 715

<210> SEQ ID NO 2
```

<211> LENGTH: 735
<212> TYPE: PRT
<213> ORGANISM: Bacillus anthracis

<400> SEQUENCE: 2

```
Glu Val Lys Gln Glu Asn Arg Leu Leu Asn Glu Ser Glu Ser Ser
1               5                   10                  15

Gln Gly Leu Leu Gly Tyr Tyr Phe Ser Asp Leu Asn Phe Gln Ala Pro
            20                  25                  30

Met Val Thr Ser Ser Thr Thr Gly Asp Leu Ser Ile Pro Ser Ser
            35                  40                  45

Glu Leu Glu Asn Ile Pro Ser Glu Asn Gln Tyr Phe Gln Ser Ala Ile
    50                  55                  60

Trp Ser Gly Phe Ile Lys Val Lys Lys Ser Asp Glu Tyr Thr Phe Ala
65                  70                  75                  80

Thr Ser Ala Asp Asn His Val Thr Met Trp Val Asp Asp Gln Glu Val
                85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125

Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
        195                 200                 205

Asn Ile His Glu Lys Lys Gly Leu Thr Lys Tyr Lys Ser Ser Pro Glu
    210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
            260                 265                 270

Lys Asn Glu Asp Gln Ser Thr Gln Asn Thr Asp Ser Gln Thr Arg Thr
        275                 280                 285

Ile Ser Lys Asn Thr Ser Thr Ser Arg Thr His Thr Ser Glu Val His
    290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
                325                 330                 335

Ser Leu Ser Leu Ala Gly Glu Arg Thr Trp Ala Glu Thr Met Gly Leu
            340                 345                 350

Asn Thr Ala Asp Thr Ala Arg Leu Asn Ala Asn Ile Arg Tyr Val Asn
        355                 360                 365

Thr Gly Thr Ala Pro Ile Tyr Asn Val Leu Pro Thr Thr Ser Leu Val
    370                 375                 380

Leu Gly Lys Asn Gln Thr Leu Ala Thr Ile Lys Ala Lys Glu Asn Gln
385                 390                 395                 400
```

```
Leu Ser Gln Ile Leu Ala Pro Asn Asn Tyr Tyr Pro Ser Lys Asn Leu
                405                 410                 415
Ala Pro Ile Ala Leu Asn Ala Gln Asp Asp Phe Ser Ser Thr Pro Ile
            420                 425                 430
Thr Met Asn Tyr Asn Gln Phe Leu Glu Leu Glu Lys Thr Lys Gln Leu
        435                 440                 445
Arg Leu Asp Thr Asp Gln Val Tyr Gly Asn Ile Ala Thr Tyr Asn Phe
    450                 455                 460
Glu Asn Gly Arg Val Arg Val Asp Thr Gly Ser Asn Trp Ser Glu Val
465                 470                 475                 480
Leu Pro Gln Ile Gln Glu Thr Thr Ala Arg Ile Ile Phe Asn Gly Lys
                485                 490                 495
Asp Leu Asn Leu Val Glu Arg Arg Ile Ala Ala Val Asn Pro Ser Asp
            500                 505                 510
Pro Leu Glu Thr Thr Lys Pro Asp Met Thr Leu Lys Glu Ala Leu Lys
        515                 520                 525
Ile Ala Phe Gly Phe Asn Glu Pro Asn Gly Asn Leu Gln Tyr Gln Gly
    530                 535                 540
Lys Asp Ile Thr Glu Phe Asp Phe Asn Phe Asp Gln Gln Thr Ser Gln
545                 550                 555                 560
Asn Ile Lys Asn Gln Leu Ala Glu Leu Asn Ala Thr Asn Ile Tyr Thr
                565                 570                 575
Val Leu Asp Lys Ile Lys Leu Asn Ala Lys Met Asn Ile Leu Ile Arg
            580                 585                 590
Asp Lys Arg Phe His Tyr Asp Arg Asn Asn Ile Ala Val Gly Ala Asp
        595                 600                 605
Glu Ser Val Val Lys Glu Ala His Arg Glu Val Ile Asn Ser Ser Thr
    610                 615                 620
Glu Gly Leu Leu Leu Asn Ile Asp Lys Asp Ile Arg Lys Ile Leu Ser
625                 630                 635                 640
Gly Tyr Ile Val Glu Ile Glu Asp Thr Glu Gly Leu Lys Glu Val Ile
                645                 650                 655
Asn Asp Arg Tyr Asp Met Leu Asn Ile Ser Ser Leu Arg Gln Asp Gly
            660                 665                 670
Lys Thr Phe Ile Asp Phe Lys Lys Tyr Asn Asp Lys Leu Pro Leu Tyr
        675                 680                 685
Ile Ser Asn Pro Asn Tyr Lys Val Asn Val Tyr Ala Val Thr Lys Glu
    690                 695                 700
Asn Thr Ile Ile Asn Pro Ser Glu Asn Gly Asp Thr Ser Thr Asn Gly
705                 710                 715                 720
Ile Lys Lys Ile Leu Ile Phe Ser Lys Lys Gly Tyr Glu Ile Gly
                725                 730                 735

<210> SEQ ID NO 3
<211> LENGTH: 2235
<212> TYPE: DNA
<213> ORGANISM: Artificial Sequence
<220> FEATURE:
<223> OTHER INFORMATION: Mature double mutant protective antigen

<400> SEQUENCE: 3
atgaaaaaac gaaaagtgtt aataccatta atggcattgt ctacgatatt agtttcaagc      60
acaggtaatt tagaggtgat tcaggcagaa gttaaacagg agaaccggtt attaaatgaa     120
tcagaatcaa gttcccaggg ttactaggaa tactatttta gtgatttgaa ttttcaagca     180
```

```
cccatggtgg ttacctcttc tactacaggg gatttatcta ttcctagttc tgagttagaa      240
aatattccat cggaaaacca atattttcaa tctgctattt ggtcaggatt tatcaaagtt      300
aagaagagtg atgaatatac atttgctact tccgctgata atcatgtaac aatgtgggta     360
gatgaccaag aagtgattaa taaagcttct aattctaaca aaatcagatt agaaaaagga     420
agattatatc aaataaaaat tcaatatcaa cgagaaaatc ctactgaaaa aggattggat     480
ttcaagttgt actggaccga ttctcaaaat aaaaagaag tgatttctag tgataactta      540
caattgccag aattaaaaca aaaatcttcg attacaagtg caggacctac ggttccagac    600
cgtgacaatg atggaatccc tgattcatta gaggtagaag gatatacggt tgatgtcaaa    660
aataaaagaa cttttctttc accatggatt tctaatattc atgaaaagaa aggattaacc    720
aaatataaat catctcctga aaaatggagc acggcttctg atccgtacag tgatttcgaa    780
aaggttacag gacggattga taagaatgta tcaccagagg caagacaccc ccttgtggca    840
gcttatccga ttgtacatgt agatatggag aatattattc tctcaaaaaa tgaggatcaa    900
tccacacaga atactgatag tcaaacgaga acaataagta aaaatacttc tacaagtagg   960
acacatacta gtgaagtagg aggagtatct gcaggattta gtaattcgaa ttcaagtacg   1020
gtcgcaattg atcattcact atctctagca ggggaaagaa cttgggctga aacaatgggt  1080
ttaaataccg ctgatacagc aagattaaat gccaatatta gatatgtaaa tactgggacg  1140
gctccaatct acaacgtgtt accaacgact tcgttagtgt taggaaaaaa tcaaacactc  1200
gcgacaatta aagctaagga aaaccaatta agtcaaatac ttgcacctaa taattattat   1260
ccttctaaaa acttggcgcc aatcgcatta aatgcacaag acgatttcag ttctactcca  1320
attacaatga attacaatca atttcttgag ttagaaaaaa cgaaacaatt aagattagat   1380
acggatcaag tatatgggaa tatagcaaca tacaattttg aaaatggaag agtgagggtg  1440
gatacaggct cgaactggag tgaagtgtta ccgcaaattc aagaaacaac tgcacgtatc  1500
attttttaatg gaaaagattt aaatctggta gaaaggcgga tagcggcggt taatcctagt   1560
gatccattag aaacgactaa accggatatg acattaaaag aagcccttaa aatagcattt   1620
ggatttaacg aaccgaatgg aaacttacaa tatcaaggga agacataac cgaatttgat   1680
tttaatttcg atcaacaaac atctcaaaat atcaagaatc agttagcgga attaaacgca   1740
actaacatat atactgtatt agataaaatc aaattaaatg caaaaatgaa tattttaata  1800
agagataaac gttttcatta tgatagaaat aacatagcag ttggggcgga tgagtcagta   1860
gttaaggagg ctcatagaga agtaattaat tcgtcaacag agggattatt gttaaatatt   1920
gataaggata taagaaaaat attatcaggt tatattgtag aaattgaaga tactgaaggg   1980
cttaaagaag ttataaatga cagatatgat atgttgaata tttctagttt acggcaagat   2040
ggaaaaacat ttatagattt taaaaaatat aatgataaat taccgttata tataagtaat   2100
cccaattata aggtaaatgt atatgctgtt actaaagaaa acactattat taatcctagt   2160
gagaatgggg atactagtac caacgggatc aagaaaattt taatcttttc taaaaaaggc   2220
tatgagatag gataa                                                    2235
```

<210> SEQ ID NO 4
<211> LENGTH: 733
<212> TYPE: PRT
<213> ORGANISM: Artificial
<220> FEATURE:
<223> OTHER INFORMATION: Variant PA-SNKE-deltaFF-E308D protein
<400> SEQUENCE: 4

-continued

```
Glu Val Lys Gln Glu Asn Arg Leu Leu Asn Glu Ser Glu Ser Ser Ser
1               5                   10                  15

Gln Gly Leu Leu Gly Tyr Tyr Phe Ser Asp Leu Asn Phe Gln Ala Pro
            20                  25                  30

Met Val Val Thr Ser Ser Thr Thr Gly Asp Leu Ser Ile Pro Ser Ser
            35                  40                  45

Glu Leu Glu Asn Ile Pro Ser Glu Asn Gln Tyr Phe Gln Ser Ala Ile
        50                  55                  60

Trp Ser Gly Phe Ile Lys Val Lys Lys Ser Asp Glu Tyr Thr Phe Ala
65                  70                  75                  80

Thr Ser Ala Asp Asn His Val Thr Met Trp Val Asp Asp Gln Glu Val
                85                  90                  95

Ile Asn Lys Ala Ser Asn Ser Asn Lys Ile Arg Leu Glu Lys Gly Arg
                100                 105                 110

Leu Tyr Gln Ile Lys Ile Gln Tyr Gln Arg Glu Asn Pro Thr Glu Lys
            115                 120                 125

Gly Leu Asp Phe Lys Leu Tyr Trp Thr Asp Ser Gln Asn Lys Lys Glu
        130                 135                 140

Val Ile Ser Ser Asp Asn Leu Gln Leu Pro Glu Leu Lys Gln Lys Ser
145                 150                 155                 160

Ser Asn Ser Ser Asn Lys Glu Ser Thr Ser Ala Gly Pro Thr Val Pro
                165                 170                 175

Asp Arg Asp Asn Asp Gly Ile Pro Asp Ser Leu Glu Val Glu Gly Tyr
                180                 185                 190

Thr Val Asp Val Lys Asn Lys Arg Thr Phe Leu Ser Pro Trp Ile Ser
            195                 200                 205

Asn Ile His Glu Lys Lys Gly Leu Thr Lys Tyr Lys Ser Ser Pro Glu
        210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
                260                 265                 270

Lys Asn Glu Asp Gln Ser Thr Gln Asn Thr Asp Ser Gln Thr Arg Thr
            275                 280                 285

Ile Ser Lys Asn Thr Thr Ser Arg Thr His Thr Ser Glu Val His
        290                 295                 300

Gly Asn Ala Asp Val His Ala Ser Asp Ile Gly Gly Ser Val Ser Ala
305                 310                 315                 320

Gly Phe Ser Asn Ser Asn Ser Ser Thr Val Ala Ile Asp His Ser Leu
                325                 330                 335

Ser Leu Ala Gly Glu Arg Thr Trp Ala Glu Thr Met Gly Leu Asn Thr
                340                 345                 350

Ala Asp Thr Ala Arg Leu Asn Ala Asn Ile Arg Tyr Val Asn Thr Gly
            355                 360                 365

Thr Ala Pro Ile Tyr Asn Val Leu Pro Thr Thr Ser Leu Val Leu Gly
        370                 375                 380

Lys Asn Gln Thr Leu Ala Thr Ile Lys Ala Lys Glu Asn Gln Leu Ser
385                 390                 395                 400

Gln Ile Leu Ala Pro Asn Asn Tyr Tyr Pro Ser Lys Asn Leu Ala Pro
                405                 410                 415

Ile Ala Leu Asn Ala Gln Asp Asp Phe Ser Ser Thr Pro Ile Thr Met
                420                 425                 430
```

```
Asn Tyr Asn Gln Phe Leu Glu Leu Glu Lys Thr Lys Gln Leu Arg Leu
            435                 440                 445

Asp Thr Asp Gln Val Tyr Gly Asn Ile Ala Thr Tyr Asn Phe Glu Asn
        450                 455                 460

Gly Arg Val Arg Val Asp Thr Gly Ser Asn Trp Ser Glu Val Leu Pro
465                 470                 475                 480

Gln Ile Gln Glu Thr Thr Ala Arg Ile Ile Phe Asn Gly Lys Asp Leu
            485                 490                 495

Asn Leu Val Glu Arg Arg Ile Ala Ala Val Asn Pro Ser Asp Pro Leu
        500                 505                 510

Glu Thr Thr Lys Pro Asp Met Thr Leu Lys Glu Ala Leu Lys Ile Ala
        515                 520                 525

Phe Gly Phe Asn Glu Pro Asn Gly Asn Leu Gln Tyr Gln Gly Lys Asp
        530                 535                 540

Ile Thr Glu Phe Asp Phe Asn Phe Asp Gln Gln Thr Ser Gln Asn Ile
545                 550                 555                 560

Lys Asn Gln Leu Ala Glu Leu Asn Ala Thr Asn Ile Tyr Thr Val Leu
            565                 570                 575

Asp Lys Ile Lys Leu Asn Ala Lys Met Asn Ile Leu Ile Arg Asp Lys
        580                 585                 590

Arg Phe His Tyr Asp Arg Asn Asn Ile Ala Val Gly Ala Asp Glu Ser
        595                 600                 605

Val Val Lys Glu Ala His Arg Glu Val Ile Asn Ser Ser Thr Glu Gly
        610                 615                 620

Leu Leu Leu Asn Ile Asp Lys Asp Ile Arg Lys Ile Leu Ser Gly Tyr
625                 630                 635                 640

Ile Val Glu Ile Glu Asp Thr Glu Gly Leu Lys Glu Val Ile Asn Asp
            645                 650                 655

Arg Tyr Asp Met Leu Asn Ile Ser Ser Leu Arg Gln Asp Gly Lys Thr
        660                 665                 670

Phe Ile Asp Phe Lys Lys Tyr Asn Asp Lys Leu Pro Leu Tyr Ile Ser
        675                 680                 685

Asn Pro Asn Tyr Lys Val Asn Val Tyr Ala Val Thr Lys Glu Asn Thr
        690                 695                 700

Ile Ile Asn Pro Ser Glu Asn Gly Asp Thr Ser Thr Asn Gly Ile Lys
705                 710                 715                 720

Lys Ile Leu Ile Phe Ser Lys Lys Gly Tyr Glu Ile Gly
            725                 730

<210> SEQ ID NO 5
<211> LENGTH: 735
<212> TYPE: PRT
<213> ORGANISM: Artificial
<220> FEATURE:
<223> OTHER INFORMATION: Variant PA-N657A protein

<400> SEQUENCE: 5

Glu Val Lys Gln Glu Asn Arg Leu Leu Asn Glu Ser Glu Ser Ser Ser
1               5                   10                  15

Gln Gly Leu Leu Gly Tyr Tyr Phe Ser Asp Leu Asn Phe Gln Ala Pro
            20                  25                  30

Met Val

-continued

```
Trp Ser Gly Phe Ile Lys Val Lys Lys Ser Asp Glu Tyr Thr Phe Ala
 65                  70                  75                  80

Thr Ser Ala Asp Asn His Val Thr Met Trp Val Asp Gln Glu Val
                 85                  90                  95

Ile Asn Lys Ala Ser Asn Ser Asn Lys Ile Arg Leu Glu Lys Gly Arg
                100                 105                 110

Leu Tyr Gln Ile Lys Ile Gln Tyr Gln Arg Glu Asn Pro Thr Glu Lys
                115                 120                 125

Gly Leu Asp Phe Lys Leu Tyr Trp Thr Asp Ser Gln Asn Lys Lys Glu
130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
                180                 185                 190

Thr Val Asp Val Lys Asn Lys Arg Thr Phe Leu Ser Pro Trp Ile Ser
                195                 200                 205

Asn Ile His Glu Lys Lys Gly Leu Thr Lys Tyr Lys Ser Ser Pro Glu
210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
                260                 265                 270

Lys Asn Glu Asp Gln Ser Thr Gln Asn Thr Asp Ser Gln Thr Arg Thr
                275                 280                 285

Ile Ser Lys Asn Thr Ser Thr Ser Arg Thr His Thr Ser Glu Val His
                290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
                325                 330                 335

Ser Leu Ser Leu Ala Gly Glu Arg Thr Trp Ala Glu Thr Met Gly Leu
                340                 345                 350

Asn Thr Ala Asp Thr Ala Arg Leu Asn Ala Asn Ile Arg Tyr Val Asn
                355                 360                 365

Thr Gly Thr Ala Pro Ile Tyr Asn Val Leu Pro Thr Thr Ser Leu Val
                370                 375                 380

Leu Gly Lys Asn Gln Thr Leu Ala Thr Ile Lys Ala Lys Glu Asn Gln
385                 390                 395                 400

Leu Ser Gln Ile Leu Ala Pro Asn Asn Tyr Tyr Pro Ser Lys Asn Leu
                405                 410                 415

Ala Pro Ile Ala Leu Asn Ala Gln Asp Asp Phe Ser Ser Thr Pro Ile
                420                 425                 430

Thr Met Asn Tyr Asn Gln Phe Leu Glu Leu Glu Lys Thr Lys Gln Leu
                435                 440                 445

Arg Leu Asp Thr Asp Gln Val Tyr Gly Asn Ile Ala Thr Tyr Asn Phe
450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
                485                 490                 495
```

```
Asp Leu Asn Leu Val Glu Arg Arg Ile Ala Ala Val Asn Pro Ser Asp
            500                 505                 510

Pro Leu Glu Thr Thr Lys Pro Asp Met Thr Leu Lys Glu Ala Leu Lys
            515                 520                 525

Ile Ala Phe Gly Phe Asn Glu Pro Asn Gly Asn Leu Gln Tyr Gln Gly
            530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
                565                 570                 575

Val Leu Asp Lys Ile Lys Leu Asn Ala Lys Met Asn Ile Leu Ile Arg
            580                 585                 590

Asp Lys Arg Phe His Tyr Asp Arg Asn Asn Ile Ala Val Gly Ala Asp
            595                 600                 605

Glu Ser Val Val Lys Glu Ala His Arg Glu Val Ile Asn Ser Ser Thr
            610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
                645                 650                 655

Ala Asp Arg Tyr Asp Met Leu Asn Ile Ser Ser Leu Arg Gln Asp Gly
            660                 665                 670

Lys Thr Phe Ile Asp Phe Lys Lys Tyr Asn Asp Lys Leu Pro Leu Tyr
            675                 680                 685

Ile Ser Asn Pro Asn Tyr Lys Val Asn Val Tyr Ala Val Thr Lys Glu
            690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
                725                 730                 735
```